(12) United States Patent
Germain et al.

(10) Patent No.: US 11,771,456 B2
(45) Date of Patent: Oct. 3, 2023

(54) ARTHROSCOPIC DEVICES AND METHODS

(71) Applicant: RELIGN Corporation, Campbell, CA (US)

(72) Inventors: Aaron Germain, San Jose, CA (US); Kyle Klein, San Jose, CA (US); Michael D. Walker, San Francisco, CA (US); Salvatore G. Mangano, San Jose, CA (US)

(73) Assignee: Relign Corporation, Campbell, CA (US)

( * ) Notice: Subject to any disclaimer, the term of this patent is extended or adjusted under 35 U.S.C. 154(b) by 1505 days.

(21) Appl. No.: 16/014,352

(22) Filed: Jun. 21, 2018

(65) Prior Publication Data

US 2018/0303509 A1 Oct. 25, 2018

Related U.S. Application Data

(62) Division of application No. 15/421,264, filed on Jan. 31, 2017, now Pat. No. 10,022,140.

(Continued)

(51) Int. Cl.
*A61B 18/14* (2006.01)
*A61B 17/32* (2006.01)
(Continued)

(52) U.S. Cl.
CPC ........ *A61B 17/32002* (2013.01); *A61B 17/16* (2013.01); *A61B 17/3205* (2013.01);
(Continued)

(58) Field of Classification Search
CPC .... A61B 2018/00208; A61B 2218/007; A61B 17/32002; A61B 18/1482; A61B 17/3205
See application file for complete search history.

(56) References Cited

U.S. PATENT DOCUMENTS

| | | |
|---|---|---|
| 2,513,564 A | 7/1950 | Ingwersen |
| 2,514,545 A | 7/1950 | Ingwersen |

(Continued)

FOREIGN PATENT DOCUMENTS

| | | |
|---|---|---|
| CN | 104093374 A | 10/2014 |
| CN | 109561908 A | 4/2019 |

(Continued)

OTHER PUBLICATIONS

Co-pending U.S. Appl. No. 16/747,801, filed Jan. 21, 2020.
(Continued)

*Primary Examiner* — Jaymi E Della
(74) *Attorney, Agent, or Firm* — SCHWEGMAN LUNDBERG & WOESSNER, P.A.

(57) ABSTRACT

A medical device includes an elongated sleeve having a longitudinal axis, a proximal end and a distal end. A cutting member having sharp edges formed from a wear-resistant ceramic material is carried at the distal end of the elongated sleeve. A motor drive is coupled to the proximal end of the elongated sleeve to rotate the sleeve at cutting member at high speed to cut bone and other hard tissue. An electrode is carried in a surface portion of ceramic cutting member for cautery or radiofrequency ablation of tissue when the sleeve and cutting member are is a stationary position.

20 Claims, 29 Drawing Sheets

Related U.S. Application Data

(60) Provisional application No. 62/324,236, filed on Apr. 18, 2016, provisional application No. 62/291,249, filed on Feb. 4, 2016.

(51) Int. Cl.
  *A61B 17/16* (2006.01)
  *A61B 17/3205* (2006.01)
  *A61B 17/00* (2006.01)
  *A61B 18/00* (2006.01)

(52) U.S. Cl.
  CPC .......... *A61B 18/1482* (2013.01); *A61B 18/14* (2013.01); *A61B 2017/0088* (2013.01); *A61B 2018/00208* (2013.01); *A61B 2018/00565* (2013.01); *A61B 2018/00577* (2013.01); *A61B 2018/00595* (2013.01); *A61B 2018/00601* (2013.01); *A61B 2217/005* (2013.01); *A61B 2218/007* (2013.01)

(56) References Cited

U.S. PATENT DOCUMENTS

| | | |
|---|---|---|
| 2,625,625 A | 1/1953 | Ingwersen |
| 2,689,895 A | 9/1954 | Ingwersen |
| 3,611,023 A | 10/1971 | Jesse, Jr. et al. |
| 3,838,242 A | 9/1974 | Goucher |
| 3,848,211 A | 11/1974 | Russell |
| 3,868,614 A | 2/1975 | Riendeau |
| 3,903,891 A | 9/1975 | Brayshaw |
| 4,060,088 A | 11/1977 | Morrison, Jr. et al. |
| 4,272,687 A | 6/1981 | Borkan |
| 4,781,175 A | 11/1988 | McGreevy et al. |
| 4,895,146 A | 1/1990 | Draenert |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,449,356 A | 9/1995 | Walbrink et al. |
| 5,490,854 A | 2/1996 | Fisher et al. |
| 5,602,449 A | 2/1997 | Krause et al. |
| 5,641,251 A | 6/1997 | Leins et al. |
| 5,669,907 A | 9/1997 | Platt, Jr. et al. |
| 5,683,366 A | 11/1997 | Eggers et al. |
| 5,720,745 A | 2/1998 | Farin et al. |
| 5,759,185 A | 6/1998 | Grinberg |
| 5,766,195 A | 6/1998 | Nobles |
| 5,776,092 A | 7/1998 | Farin et al. |
| 5,810,809 A | 9/1998 | Rydell et al. |
| 5,823,971 A | 10/1998 | Robinson et al. |
| 5,839,897 A | 11/1998 | Bordes |
| 5,849,010 A | 12/1998 | Wurzer et al. |
| 5,857,995 A | 1/1999 | Thomas et al. |
| 5,873,855 A | 2/1999 | Eggers et al. |
| 5,888,198 A | 3/1999 | Eggers et al. |
| 5,891,095 A | 4/1999 | Eggers et al. |
| 5,904,681 A | 5/1999 | West, Jr. |
| 5,913,867 A | 6/1999 | Dion |
| 5,964,752 A | 10/1999 | Stone |
| 5,989,248 A | 11/1999 | Tu et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,210,405 B1 | 4/2001 | Goble et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,245,084 B1 | 6/2001 | Mark et al. |
| 6,261,241 B1 | 7/2001 | Burbank et al. |
| 6,296,636 B1 | 10/2001 | Cheng et al. |
| 6,332,886 B1 | 12/2001 | Green et al. |
| 6,348,051 B1 | 2/2002 | Farin et al. |
| 6,358,263 B2 | 3/2002 | Mark et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,419,684 B1 | 7/2002 | Heisler et al. |
| 6,443,948 B1 | 9/2002 | Suslov |
| 6,475,215 B1 | 11/2002 | Tanrisever |
| 6,514,250 B1* | 2/2003 | Jahns ................ A61B 18/1492 606/41 |
| 6,538,549 B1 | 3/2003 | Renne et al. |
| 6,579,289 B2 | 6/2003 | Schnitzler |
| 6,610,059 B1* | 8/2003 | West, Jr. ............. A61B 18/148 606/41 |
| 6,632,220 B1 | 10/2003 | Eggers et al. |
| 6,656,195 B2 | 12/2003 | Peters et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,783,533 B2 | 8/2004 | Green et al. |
| 6,821,275 B2 | 11/2004 | Truckai et al. |
| 6,837,884 B2 | 1/2005 | Woloszko |
| 6,890,332 B2 | 5/2005 | Truckai et al. |
| 6,902,564 B2 | 6/2005 | Morgan et al. |
| 6,979,332 B2 | 12/2005 | Adams |
| 7,087,054 B2 | 8/2006 | Truckai et al. |
| 7,150,747 B1 | 12/2006 | McDonald et al. |
| 7,220,261 B2 | 5/2007 | Truckai et al. |
| 7,309,849 B2 | 12/2007 | Truckai et al. |
| 7,549,989 B2 | 6/2009 | Morgan et al. |
| 7,674,263 B2 | 3/2010 | Ryan et al. |
| 7,678,069 B1 | 3/2010 | Baker et al. |
| 7,713,269 B2 | 5/2010 | Auge, II et al. |
| 7,717,710 B2 | 5/2010 | Danger et al. |
| 7,744,595 B2 | 6/2010 | Truckai et al. |
| 7,771,422 B2 | 8/2010 | Auge, II et al. |
| 7,819,861 B2 | 10/2010 | Auge, II et al. |
| 7,819,864 B2 | 10/2010 | Morgan et al. |
| 7,955,331 B2 | 6/2011 | Truckai et al. |
| 8,012,153 B2 | 9/2011 | Woloszko et al. |
| 8,016,823 B2 | 9/2011 | Shadduck |
| 8,062,319 B2 | 11/2011 | O'Quinn et al. |
| 8,075,555 B2 | 12/2011 | Truckai et al. |
| 8,192,424 B2 | 6/2012 | Woloszko |
| 8,192,428 B2 | 6/2012 | Truckai et al. |
| 8,221,404 B2 | 7/2012 | Truckai |
| 8,323,280 B2 | 12/2012 | Germain et al. |
| 8,333,763 B2 | 12/2012 | Truckai et al. |
| 8,486,096 B2 | 7/2013 | Robertson et al. |
| 8,702,702 B1 | 4/2014 | Edwards et al. |
| 9,179,923 B2 | 11/2015 | Gubellini et al. |
| 9,204,918 B2 | 12/2015 | Germain et al. |
| 9,277,954 B2 | 3/2016 | Germain et al. |
| 9,504,521 B2 | 11/2016 | Deutmeyer et al. |
| 9,585,675 B1 | 3/2017 | Germain et al. |
| 9,592,085 B2 | 3/2017 | Germain et al. |
| 9,603,656 B1 | 3/2017 | Germain et al. |
| 9,681,913 B2 | 6/2017 | Orczy-Timko et al. |
| 9,795,434 B2 | 10/2017 | Germain et al. |
| 10,022,140 B2 | 7/2018 | Germain et al. |
| 10,327,842 B2 | 6/2019 | Germain et al. |
| 10,568,685 B2 | 2/2020 | Germain et al. |
| 10,582,966 B2 | 3/2020 | Orczy-Timko et al. |
| 2003/0014051 A1 | 1/2003 | Woloszko |
| 2003/0083681 A1 | 5/2003 | Moutafis et al. |
| 2003/0125727 A1 | 7/2003 | Truckai et al. |
| 2003/0163135 A1 | 8/2003 | Hathaway |
| 2004/0044341 A1 | 3/2004 | Truckai et al. |
| 2004/0167427 A1 | 8/2004 | Quick et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |

(56) References Cited

U.S. PATENT DOCUMENTS

| | | | |
|---|---|---|---|
| 2006/0074345 A1 | 4/2006 | Hibner | |
| 2006/0178670 A1 | 8/2006 | Woloszko et al. | |
| 2006/0200123 A1 | 9/2006 | Ryan | |
| 2006/0224154 A1 | 10/2006 | Shadduck et al. | |
| 2007/0213704 A1 | 9/2007 | Truckai et al. | |
| 2008/0003255 A1 | 1/2008 | Kerr et al. | |
| 2008/0103494 A1 | 5/2008 | Rioux et al. | |
| 2008/0188848 A1 | 8/2008 | Deutmeyer et al. | |
| 2008/0208249 A1 | 8/2008 | Blain et al. | |
| 2009/0048485 A1 | 2/2009 | Heisler | |
| 2009/0076498 A1 | 3/2009 | Saadat et al. | |
| 2009/0270849 A1 | 10/2009 | Truckai et al. | |
| 2010/0100091 A1 | 4/2010 | Truckai | |
| 2010/0305565 A1 | 12/2010 | Truckai et al. | |
| 2011/0282373 A1 | 11/2011 | Chekan et al. | |
| 2012/0209112 A2 | 8/2012 | Patel et al. | |
| 2012/0245580 A1 | 9/2012 | Germain et al. | |
| 2012/0330292 A1 | 12/2012 | Shadduck et al. | |
| 2013/0046304 A1 | 2/2013 | Germain et al. | |
| 2013/0085498 A1* | 4/2013 | Matusaitis | A61B 17/32002 606/180 |
| 2013/0122461 A1 | 5/2013 | Shioiri | |
| 2013/0172870 A1 | 7/2013 | Germain et al. | |
| 2013/0253498 A1* | 9/2013 | Germain | A61B 90/08 606/28 |
| 2013/0267937 A1 | 10/2013 | Shadduck et al. | |
| 2013/0296847 A1 | 11/2013 | Germain et al. | |
| 2013/0296849 A1 | 11/2013 | Germain et al. | |
| 2013/0317493 A1 | 11/2013 | Truckai et al. | |
| 2013/0331833 A1* | 12/2013 | Bloom | A61B 18/1445 606/45 |
| 2014/0100567 A1 | 4/2014 | Edwards et al. | |
| 2014/0135806 A1 | 5/2014 | Shener-Irmakoglu et al. | |
| 2014/0336643 A1 | 11/2014 | Orczy-Timko et al. | |
| 2015/0245862 A1 | 9/2015 | Goode et al. | |
| 2015/0265337 A1 | 9/2015 | Bloom | |
| 2016/0346036 A1 | 12/2016 | Orczy-Timko et al. | |
| 2017/0128083 A1 | 5/2017 | Germain et al. | |
| 2017/0172648 A1 | 6/2017 | Germain et al. | |
| 2017/0224368 A1 | 8/2017 | Germain et al. | |
| 2017/0252099 A1 | 9/2017 | Orczy-Timko et al. | |
| 2018/0263649 A1 | 9/2018 | Germain et al. | |
| 2019/0015151 A1 | 1/2019 | Germain et al. | |
| 2020/0060752 A1 | 2/2020 | Germain et al. | |
| 2020/0163710 A1 | 5/2020 | Germain et al. | |

FOREIGN PATENT DOCUMENTS

| | | |
|---|---|---|
| DE | 102005059864 A1 | 6/2007 |
| EP | 1034747 A1 | 9/2000 |
| EP | 3410961 A1 | 12/2018 |
| JP | H11146883 A | 6/1999 |
| JP | 2002509756 A | 4/2002 |
| JP | 2002538933 A | 11/2002 |
| JP | 2014534874 A | 12/2014 |
| JP | 2015180290 A | 10/2015 |
| JP | 2019510535 A | 4/2019 |
| WO | WO-9949799 A1 | 10/1999 |
| WO | WO-0053112 A2 | 9/2000 |
| WO | WO-0062685 A1 | 10/2000 |
| WO | WO-0053112 A3 | 12/2000 |
| WO | WO-0124720 A1 | 4/2001 |
| WO | WO-2007073867 A1 | 7/2007 |
| WO | WO-2013052250 A1 | 4/2013 |
| WO | WO-2016171963 A1 | 10/2016 |
| WO | WO-2017070486 A1 | 4/2017 |
| WO | WO-2017070510 A1 | 4/2017 |
| WO | WO-2017136414 A1 | 8/2017 |

OTHER PUBLICATIONS

Co-pending U.S. Appl. No. 16/780,041, filed Feb. 3, 2020.
European search report and opinion dated May 15, 2019 for EP Application No. 16858321.9.
European search report and opinion dated Jul. 12, 2019 for EP Application No. 17748056.3.
Notice of allowance dated Feb. 4, 2019 for U.S. Appl. No. 15/449,796.
Notice of allowance dated Mar. 7, 2019 for U.S. Appl. No. 15/449,796.
Notice of Allowance dated Oct. 17, 2019 for U.S. Appl. No. 15/415,721.
Notice of Allowance dated Nov. 1, 2019 for U.S. Appl. No. 15/599,372.
Office action dated Apr. 27, 2020 for U.S. Appl. No. 15/920,130.
Office action dated May 8, 2019 for U.S. Appl. No. 15/415,721.
Office action dated Dec. 12, 2018 for U.S. Appl. No. 15/415,721.
Co-pending U.S. Appl. No. 15/855,684, filed Dec. 27, 2017.
European search report dated Nov. 2, 2009 for EP Application No. 01967968.7.
International search report and opinion dated Jul. 15, 2016 for PCT/US2016/027157.
International Search Report and Written Opinion dated Mar. 8, 2017 for International PCT Patent Application No. PCT/US2016/058179.
International Search Report and Written Opinion dated May 16, 2017 for International PCT Patent Application No. PCT/US2017/016002.
International Search Report and Written Opinion dated May 23, 2012 for International PCT Patent Application No. PCT/US2012/023390.
International Search Report and Written Opinion dated Nov. 29, 2016 for International Application No. PCT/US2016/058145.
International search report dated Jan. 14, 2002 for PCT/US2001/025409.
Kim, et al. Optical feedback signal for ultra short pulse ablation of tissue. Appl. Surface Sci. 1998; 127-129:857-862.
Notice of Allowance dated Jan. 6, 2017 for U.S. Appl. No. 14/960,084.
Notice of Allowance dated Feb. 8, 2017 for U.S. Appl. No. 14/977,256.
Notice of Allowance dated Feb. 16, 2017 for U.S. Appl. No. 15/096,546.
Notice of allowance dated Mar. 19, 2018 for U.S. Appl. No. 15/421,264.
Notice of Allowance dated Dec. 2, 2016 for U.S. Appl. No. 14/977,256.
Notice of Allowance dated Dec. 30, 2016 for U.S. Appl. No. 14/977,256.
Office action dated May 3, 2016 for U.S. Appl. No. 14/960,084.
Office action dated Jul. 6, 2018 for U.S. Appl. No. 15/449,796.
Office Action dated Jul. 21, 2017 for U.S. Appl. No. 15/421,264.
Office action dated Jul. 28, 2016 for U.S. Appl. No. 14/977,256.
Office Action dated Aug. 18, 2016 for U.S. Appl. No. 14/960,084.
Office Action dated Sep. 26, 2016 for U.S. Appl. No. 15/096,546.
Office action dated Nov. 3, 2017 for U.S. Appl. No. 15/449,796.
Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.
Tucker et al. Histologic characteristics of electrosurgical injuries. J. Am. Assoc. Gyneco. Laproscopy. 1997; 4(2):857-862.
Volpato, et al., Application of Zirconia in Dentistry: Biological, Mechanical and Optical Considerations. Advances in ceramics—electric and magnetic ceramics, bioceramics, ceramics and environment. Sep. 2011.
"U.S. Appl. No. 14/977,256, Corrected Notice of Allowability dated Dec. 30, 2016", 7 pgs.
"U.S. Appl. No. 15/421,264, Response filed Jan. 8, 2018 to Non Final Office Action dated Jul. 21, 2017", 7 pgs.
"U.S. Appl. No. 15/421,264, Response filed Jul. 11, 2017 to Restriction Requirement dated Jun. 1, 2017", 1 pg.
"U.S. Appl. No. 15/421,264, Restriction Requirement dated Jun. 1, 2017", 11 pgs.
"Chinese Application Serial No. 201780022226.3, Notification to Make Divisional Application dated Oct. 23, 2020", (W/ English Translation), 3 pgs.
"Chinese Application Serial No. 201780022226.3, Office Action dated Oct. 23, 2018", (W/ English Translation), 2 pgs.
"European Application Serial No. 17748056.3, Communication Pursuant to Article 94(3) EPC dated Mar. 24, 2020", 5 pgs.

(56) References Cited

OTHER PUBLICATIONS

"European Application Serial No. 17748056.3, Response filed Jan. 30, 2020 to Extended European Search Report dated Jul. 12, 2019", 40 pgs.

"European Application Serial No. 17748056.3, Response filed Jul. 29, 2020 to Communication Pursuant to Article 94(3) EPC dated Mar. 24, 2020", 22 pgs.

"International Application Serial No. PCT/US2017/016002, International Preliminary Report on Patentability dated Aug. 16, 2018", 8 pgs.

"Japanese Application Serial No. 2018-540865, Notification of Reasons for Refusal dated Dec. 25, 2020", (W/ English Translation), 10 pgs.

\* cited by examiner

ARTHROSCOPIC DEVICES AND METHODS

CROSS-REFERENCE TO RELATED APPLICATIONS

This application is a divisional of U.S. patent application Ser. No. 15/421,264, filed Jan. 31, 2017, now U.S. Pat. No. 10,022,140, which claims the benefit of provisional application nos. 62/291,249, filed on Feb. 4, 2016, and 62/324, 236, tiled on Apr. 18, 2016, the full disclosures of which are incorporated herein by reference.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments configured for cutting and removing tissue with a ceramic cutting member and/or electrosurgically treating tissue with an electrode carried by the ceramic cutting member.

2. Description of the Background Art

In several surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove tissue for such procedures. A typical arthroscopic shaver or burr comprises a metal cutting member carried at the distal end of a metal sleeve that rotates within an open-ended metal shaft. A suction pathway for removal of bone fragments or other tissues is provided through a window proximal to the metal cutting member that communicates with a lumen in the sleeve.

When metal shavers and burrs "wear" during a procedure, which occurs very rapidly when cutting bone, the wear can be accompanied by loss of micro-particles from fracture and particle release which occurs along with dulling due to metal deformation. In such surgical applications, even very small amounts of such foreign particles that are not recovered from a treatment site can lead to detrimental effects on the patient health, with inflammation being typical. In some cases, the foreign particles can result in joint failure due to osteolysis, a term used to define inflammation due to presence of such foreign particles. A recent article describing such foreign particle induced inflammation is Pedowitz, et al. (2013) Arthroscopic surgical tools: "A source of metal particles and possible joint damage", Arthroscopy—The Journal of Arthroscopic and Related Surgery, 29(9), 1559-1565. In addition to causing inflammation, the presence of metal particles in a joint or other treatment site can cause serious problems for future MRIs. Typically, the MRI images will be blurred by agitation of the metal particles caused by the magnetic field used in the imaging, making assessments of the treatment difficult.

Another problem with the currently available metal shavers/burrs relates to manufacturing limitations in combination with the rapid dulling of metal cutting edges. Typically, a metal cutter is manufactured by machining the cutting surfaces and flutes into a burr or abrader surface. The flute shape and geometry can be limited since it is dictated by the machining process, and burr size and shape limitations may direct usage toward more coarse bone removal applications. Further, when operated in a rotational or oscillatory mode, the cutting edges adapted for coarse bone removal may have a kickback effect as the flutes first make contact with bone, which is aggravated by rapid dulling of the machined cutting edges.

Therefore, the need exists for arthroscopic burrs and/or shavers that can operate to cut and remove bone without the release of fractured particles and micro-particles into the treatment site. Further, there is a need for burrs/cutters that do not wear rapidly and that can have cutting edges not limited by metal machining techniques.

As an alternative to such arthroscopic cutters and shavers, another class of tissue removal tools relies on radiofrequency (RF) ablation to remove the soft tissue. Tools such as those described in U.S. Pat. Nos. 6,149,620 and 7,678,069 can be highly effective in volumetric removal of soft tissue in the knee and elsewhere but are ineffective in resecting bone.

Therefore, the need exists for tools that can effectively remove both bone and soft tissue and which can combine the advantages of both cutter-based hard tissue resection and RF-based soft tissue ablation. At least some of these objectives will be met by the inventions described below.

SUMMARY OF THE INVENTION

The present invention provides a variety of improved tissue removal devices and methods, including devices and methods which can remove tissue by cutting (resection) and/or by radiofrequency (RF) ablation.

In a first specific aspect of the present invention, a medical device for removing tissue includes an elongated sleeve having a longitudinal axis, a proximal end, and a distal end. A ceramic cutting member with at least one cutting edge extends distally from the distal end of the elongated sleeve, and an electrode is carried by the cutting member. A motor drive is configured to couple to the proximal end of elongated sleeve to rotate the cutting member. In some embodiments, the elongated sleeve is an inner sleeve and is coaxially and rotatably disposed in an outer sleeve, where the outer sleeve may have a cut-out to expose the ceramic cutting member and the electrode.

The cutting edge of medical device for removing tissue will have a radially outward rotational periphery which is at least as great as an outward rotational periphery of the electrode, and the dielectric material typically comprises a wear-resistant ceramic material, usually consisting exclusively of the wear-resistant ceramic material. Exemplary wear-resistant ceramic materials are selected from the group consisting of yttria-stabilized zirconia, magnesia-stabilized zirconia, ceria-stabilized zirconia, zirconia toughened alumina and silicon nitride. The medical device will typically further comprise an RF source connected to the electrode and a controller operatively connectable to the motor drive, the RF source, and a negative pressure source.

The cutting member of the medical device will often have at least one window in a side thereof which communicates with an interior channel of the elongated (inner) sleeve which is configured to be connected to a negative pressure source. The window is typically adjacent to the electrode so that material released by resection and/or ablation can be aspirated through said window. The window optionally can be used for fluid infusion for use in electrosurgery. In some instances, the window is proximal to the electrode and/or proximal to the cutting edges, an/or at least partly intermediate the cutting edges. The cutting member may have from 1 to 100 cutting edges, a diameter ranging between 2 mm and 10 mm, and may extend over an axial length ranging between 1 mm and 10 mm. The cutting edges may be arranged in a pattern selected from at least one of helical, angled and straight relative to said axis.

In a second specific aspect of the present invention, a medical system for removing tissue includes an elongated rotatable shaft with a distal tip comprising (or composed of) a ceramic material. A motor drive is configured to rotate the shaft and the distal tip, and an electrode is carried by the distal tip. The electrode is coupled to an RF source, and a controller is operatively connected to the motor drive and to the RF source. The controller is configured to stop rotation of the shaft in a selected position, such as a position that will expose the electrode in a position that allows it to be used for ablative or other tissue treatment.

The medical device may further include a sensor configured to sense a rotational position of the shaft and to send signals to the controller indicating said rotational position. The controller may be configured to stop rotation of the shaft in the selected or other position, for example when a portion of distal tip such as the electrode or cutter element is properly oriented to perform a desired ablation, resection, or other treatment. The sensor is usually a Hall sensor. The controller may be further configured to control delivery of RF energy to the electrode when the shaft in said selected position. The distal tip of the rotatable shaft may have at least one window in a side thereof that opens to an interior channel in the shaft where the channel is configured to communicate with a negative pressure source. The window may be adjacent the electrode and/or may be at least partly proximal to the electrode. The distal tip may comprise or consist entirely of a wear-resistant ceramic material, such as those listed elsewhere herein.

In a third specific aspect of the present invention, a medical device for removing tissue includes an elongated shaft with a distal tip having a ceramic member. A window in the ceramic member connects to an interior channel in the shaft, and an electrode in the ceramic member is positioned adjacent to the window. The interior channel is configured to be coupled to a negative pressure source.

The electrode is usually disposed distally of the window, and the electrode may have a width equal to at least 50% of a width of the window, sometimes being at least 80% of the width of the window, and sometimes being at least 100% of the width of the window, or greater. At least one side of the window may have a sharp edge, and the electrode may at least partly encircle the distal end of the window. The ceramic member may have at least one sharp edge for cutting tissue, and a radially outward surface of the ceramic member usually defines a cylindrical periphery with an outward surface of the electrode being within said cylindrical periphery. The ceramic member will usually have at least one and more usually a plurality of sharp edges for cutting tissue.

In a fourth specific aspect of the present invention, a method for electrosurgical tissue ablation comprises providing an elongated shaft with a working end including an active electrode carried adjacent to a window that opens to an interior channel in the shaft. The channel is connected to a negative pressure source, and the active electrode and window are positioned in contact with target tissue in a fluid-filled space. The negative pressure source may be activated to suction the target tissue into the window, and the active electrode is activated (typically to deliver RF energy) to ablate tissue while translating the working end relative to the targeted tissue.

In specific aspects of the methods, a motor drive rotates the shaft and the distal tip (typically at at least 3,000 rpm), and a controller operatively connects the interior channel to the negative pressure source and an RF source to the electrode. The ceramic member is a wear-resistant material, typically as noted previously herein. Tissue debris is aspirated through the interior channel, and the working end is translated to remove a surface portion of the targeted tissue and/or to undercut the targeted tissue to thereby remove chips of tissue.

In still further aspects, the present invention provides a high-speed rotating cutter or burr that is fabricated entirely of a ceramic material. In one variation, the ceramic is a molded monolith with sharp cutting edges and is adapted to be motor driven at speeds ranging from 3,000 rpm to 20,000 rpm. The ceramic cutting member is coupled to an elongate inner sleeve that is configured to rotate within a metal, ceramic or composite outer sleeve. The ceramic material is exceptionally hard and durable and will not fracture and thus not leave foreign particles in a treatment site. In one aspect, the ceramic has a hardness of at least 8 GPa (kg/mm$^2$) and a fracture toughness of at least 2 MPam$^{1/2}$. The "hardness" value is measured on a Vickers scale and "fracture toughness" is measured in MPam$^{1/2}$. Fracture toughness refers to a property which describes the ability of a material containing a flaw to resist further fracture and expresses a material's resistance to such fracture. In another aspect, it has been found that materials suitable for the cutting member of the invention have a certain hardness-to-fracture toughness ratio, which is a ratio of at least 0.5 to 1

While the cutting assembly and ceramic cutting member of the invention have been designed for arthroscopic procedures, such devices can be fabricated in various cross-sections and lengths and can be use in other procedures for cutting bone, cartilage and soft tissue such as in ENT procedures, spine and disc procedures and plastic surgeries.

In another aspect, the present invention provides a medical device that includes an elongated sleeve having a longitudinal axis, a proximal end and a distal end. A cutting member extends distally from the distal end of the elongated sleeve, and has sharp cutting edges. The cutting head is formed from a wear-resistant ceramic material, and a motor coupled to the proximal end of elongated sleeve rotates the cutting member. The cutter may be engaged against bone and rotated to cut bone tissue without leaving any foreign particles in the site.

The wear-resistant ceramic material may comprise any one or combination of (1) zirconia, (2) a material selected from the group of yttria-stabilized zirconia, magnesia-stabilized zirconia and zirconia toughened alumina, or (3) silicon nitride. The cutting member typically has from 2 to 100 cutting edges, a cylindrical periphery, and is usually rounded in the distal direction. The cutting member will typically have diameter ranging from 2 mm to 10 mm, and the cutting edges will typically extend over an axial length ranging between 1 mm and 10 mm. The cutting edges may be any one of helical, angled or straight relative to said axis, and flutes between the cutting edges usually have a depth ranging from 0.10 mm to 2.5 mm. An aspiration tube may be configured to connect to a negative pressure source, where the cutting member has at least one window in a side thereof which opens to a hollow interior. In these embodiments, the hollow interior is open to a central passage of the elongated member which is connected to the aspiration tube.

In a further aspect, the present invention provides a medical device for treating bone including an elongated shaft having a longitudinal axis, a proximal end, and a distal end. A monolithic cutting member fabricated of a material having a hardness of at least 8 GPa (kg/mm$^2$) is coupled to the distal end of the elongated shaft, and a motor is operatively connected to the proximal end of the shaft, said motor being configured to rotate the shaft at at least 3,000 rpm.

The material usually has a fracture toughness of at least 2 MPam$^{1/2}$, and further usually has a coefficient of thermal expansion of less than 10 (1×10$^6$/° C.). The material typically comprises a ceramic selected from the group of yttria-stabilized zirconia, magnesia-stabilized zirconia, ceria-stabilized zirconia, zirconia toughened alumina and silicon nitride, and the cutting member typically has a cylindrical periphery and an at least partly rounded periphery in an axial direction.

In a still further aspect, the present invention provides a medical device for treating bone comprising a monolithic cutting member fabricated of a material having a hardness-to-fracture toughness ratio of at least 0.5:1, usually at least 0.8:1, and often at least 1:1.

In yet another aspect, the present invention provides a medical device for cutting tissue including a motor-driven shaft having a longitudinal axis, a proximal end, a distal end, and a lumen extending therebetween. A rotatable cutting member is fabricated entirely of a ceramic material and is operatively coupled to the distal end of the motor-driven shaft. At least one window in the cutting member communicates with the lumen in the shaft, and a negative pressure source is in communication with the lumen to remove cut tissue from an operative site.

The ceramic material typically has a hardness of at least 8 GPa (kg/mm$^2$) and a fracture toughness of at least 2 MPam$^{1/2}$. Additionally, the ceramic material will usually have a coefficient of thermal expansion of less than 10 (1×10$^6$/° C.). Exemplary ceramic materials are selected from the group consisting of yttria-stabilized zirconia, magnesia-stabilized zirconia, ceria-stabilized zirconia, zirconia toughened alumina and silicon nitride, and the cutting member usually has cutting edges where the at least one window is proximate to the cutting edges, and the at least one window is in at least one flute between the cutting edges.

In another aspect, the present invention provides a method for preventing foreign particle induced inflammation at a bone treatment site. A rotatable cutter fabricated of a ceramic material having a hardness of at least 8 GPa (kg/mm$^2$) and a fracture toughness of at least 2 MPam$^{1/2}$ is engaged against bone and rotated to cut bone tissue without leaving any foreign particles in the site.

The ceramic material is usually selected from the group consisting of yttria-stabilized zirconia, magnesia-stabilized zirconia, ceria-stabilized zirconia, zirconia toughened alumina and silicon nitride, and the cutter is typically rotated at 10,000 rpm or greater. Cut bone tissue is removed from the bone treatment site through a channel in the cutter, typically by aspirating the cut bone tissue through the channel.

In a first specific aspect of the present invention, a device for removing tissue in a patient comprises a shaft having a longitudinal axis. The shaft includes (1) an outer sleeve having a distal region with an outer window and an axial bore therethrough and (2) an inner sleeve axis rotationally disposed in the axial bore of the outer sleeve. A dielectric cutting member having a longitudinal axis is carried at a distal end of the inner sleeve, and the dielectric cutting member has an inner window with at least one sharp cutting edge. An electrode is disposed on an exterior surface of the cutting member so that the inner sleeve can be rotated by a motor or otherwise relative to the outer sleeve to expose the electrode through the outer window of the outer sleeve.

The cutting member is usually cylindrical, and the inner window typically has two circumferentially spaced-apart edges wherein at least one of said edges carries or defines the sharp cutting edge. Often, each of the two circumferentially spaced-apart window edges defines or carries a sharp cutting edge. In many embodiments, the electrode is an elongate electrode aligned longitudinally with the axis of the cutting member. The elongate electrode is typically circumferentially spaced-apart from the at least one sharp cutting edge of the inner window.

Such medical device usually will include a motor drive configured to be detachably coupled to the shaft to rotate the inner sleeve and the cutting member relative to the outer sleeve. The motor drive usually includes a controller configured automatically stopping rotation of the inner sleeve and cutting member relative to the outer sleeve to position the electrode within said outer window.

A rotational position sensor that senses the relative rotational positions of the inner sleeve and the outer sleeve may be employed to deliver the positional information to the controller, and the controller may use the positional information to position the inner sleeve and cutting member relative to the outer sleeve to position the electrode within said outer window.

In specific embodiment, the cutter member may comprise an electrically insulating ceramic material, and the inner and outer sleeves of the shaft may comprise an electrically conductive metal. In such designs, an electrically insulating layer will be disposed between an interior surface of the axial bore of the outer sleeve and an exterior surface of the inner sleeve. An electrically conductive inner sleeve allows the electrode to be electrically coupled to the controller and associated electrosurgical power supply via the inner sleeve.

In a second specific aspect of the present invention, a method for removing tissue in a patient comprises positioning a distal end of a shaft at a tissue target site so that an outer window of an outer sleeve of the shaft is engaged against a target tissue. An inner window of a ceramic cutting member carried by an inner sleeve of the shaft is counter-rotated relative to the outer window of the outer sleeve of the shaft to shear target tissue which penetrates through the windows. Rotation of the inner and outer sleeves may be stopped to expose an electrode on the ceramic cutting member in the outer window. The exposed electrode may then be engaged against target tissue, and electrical current delivered through the electrode to the target tissue engaged by the electrode.

The electrical current is usually a radiofrequency current, and the electrical current may be delivered to cauterize or ablate tissue. As a particular advantage, the electrical current may be delivered to cauterize tissue at a location where tissue had been sheared by the counter-rotating windows.

In a still further aspect of the present invention, a medical shaver device for removing tissue comprising inner and outer concentric sleeves extending to a working end with a distal tissue cutting member. A light emitter carried by the working end. The light emitter may be carried by the inner sleeve, may be carried by the outer sleeve, or in some instances could be carried by or span both the inner and outer sleeves The light emitter is typically a light emitting diode.

In yet another aspect of the present invention, a method for removing tissue comprising providing a tissue cutter having a light-emitting source at an end adjacent to a tissue cutting member. A target tissue is exposed to light emitted from the light-emitting source on the tissue cutter so that light passes through the target tissue. Tissue characteristics can be determined based upon the observed light which passes through the tissue, and the tissue can be cut with the tissue cutter based upon the observed tissue characteristics. Salient tissue characteristics may be assessed based upon the observed tissue translucence and include any one of a thickness of an anatomic structures, a cutting depth, and a location of adjacent anatomic structures, and the like.

In alternative embodiments of the device, a single elongated sleeve may be provided and used to remove tissue. The single elongated sleeve may be used without a second sleeve and carries a dielectric cutting member extending distally from a distal end of the sleeve. A window with at least one sharp cutting edge is disposed in or on the cutting member, and an electrode is also carried by the cutting member, typically being circumferentially spaced-apart from the window. The device typically further includes a motor drive configured to couple to a proximal end of the elongated sleeve to rotate the cutting member.

In other aspects of the present invention, the electrodes may have a plurality of micropores or microchannels therein configured to communicate with a negative pressure source, typically via a central channel in ceramic body and/or a bore through an associated sleeve. During use of a working end in a saline-submerged working space, typically when the electrode is energized to coagulate or ablate tissue, the negative pressure source can be actuated to draw fluid through the microchannels of the electrode to inhibit or eliminate bubble formation about the electrode surface which can significantly improve endoscopic viewing of the targeted treatment site.

In yet another aspect of the present invention, a robust and economical connection between the ceramic body the associated metal sleeve can be made without on adhesive bonds, brazing or the like. A metal collar, typically having a thin wall, has openings or slots for receiving projecting features formed on a reduced diameter proximal region of the ceramic body. Each receiving opening typically has a first longitudinal surface and a second longitudinal surface that interface with longitudinal surfaces of the projecting features. The collar can have an axial discontinuity or break to allow it to circumferentially open or flex apart to be placed over the projecting features on the proximal region of the ceramic body. The outer diameter of the metal collar is typically dimensioned to fit into a bore of the inner sleeve. After assembly, the metal sleeve can be permanently welded to the metal collar, e.g. by laser welding from the exterior of metal sleeve.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and removal devices and related methods of use. Several variations of the invention will now be described to provide an overall understanding of the principles of the form, function and methods of use of the devices disclosed herein. In general, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, the present invention provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 rpm to 20,000 rpm.

Figure 1:
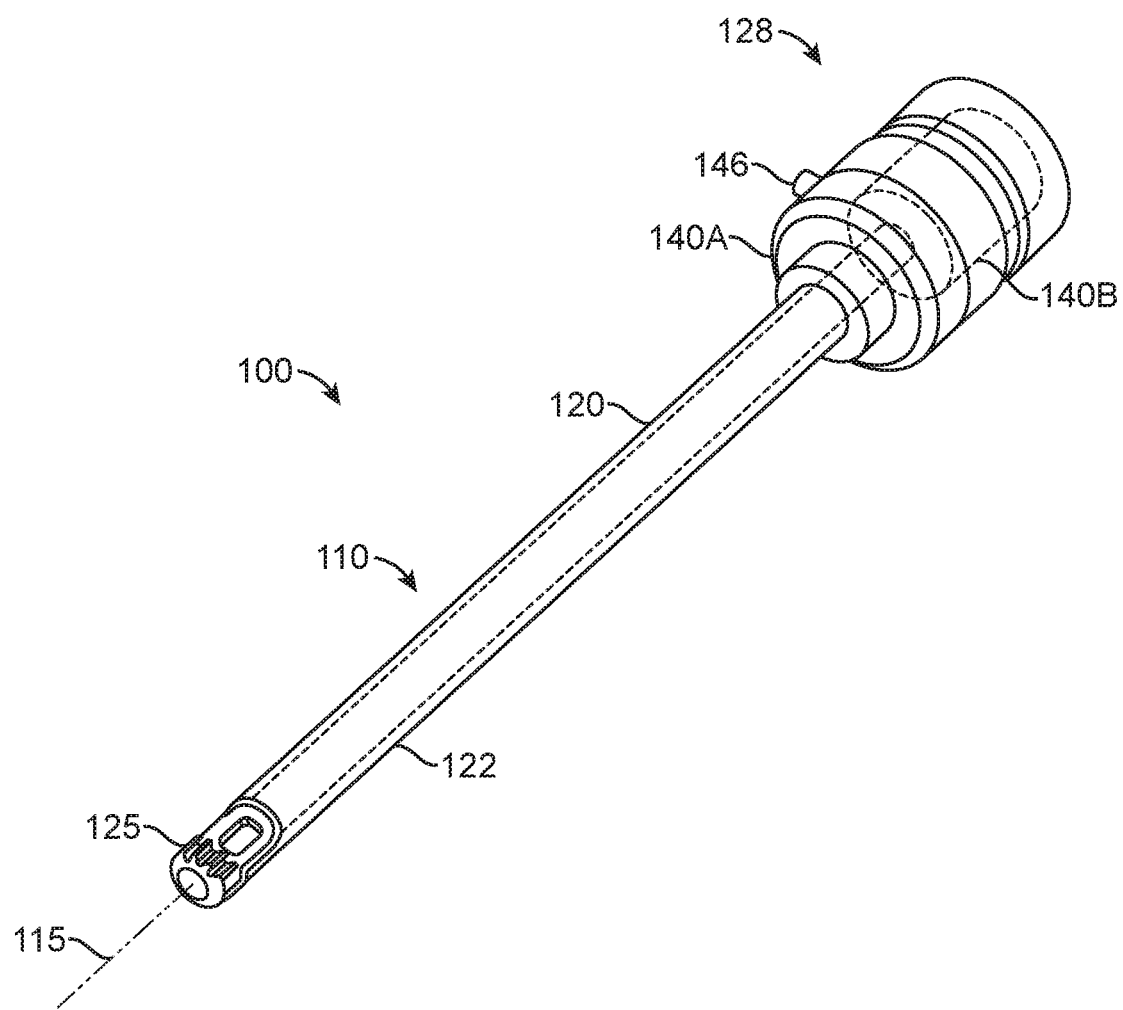
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
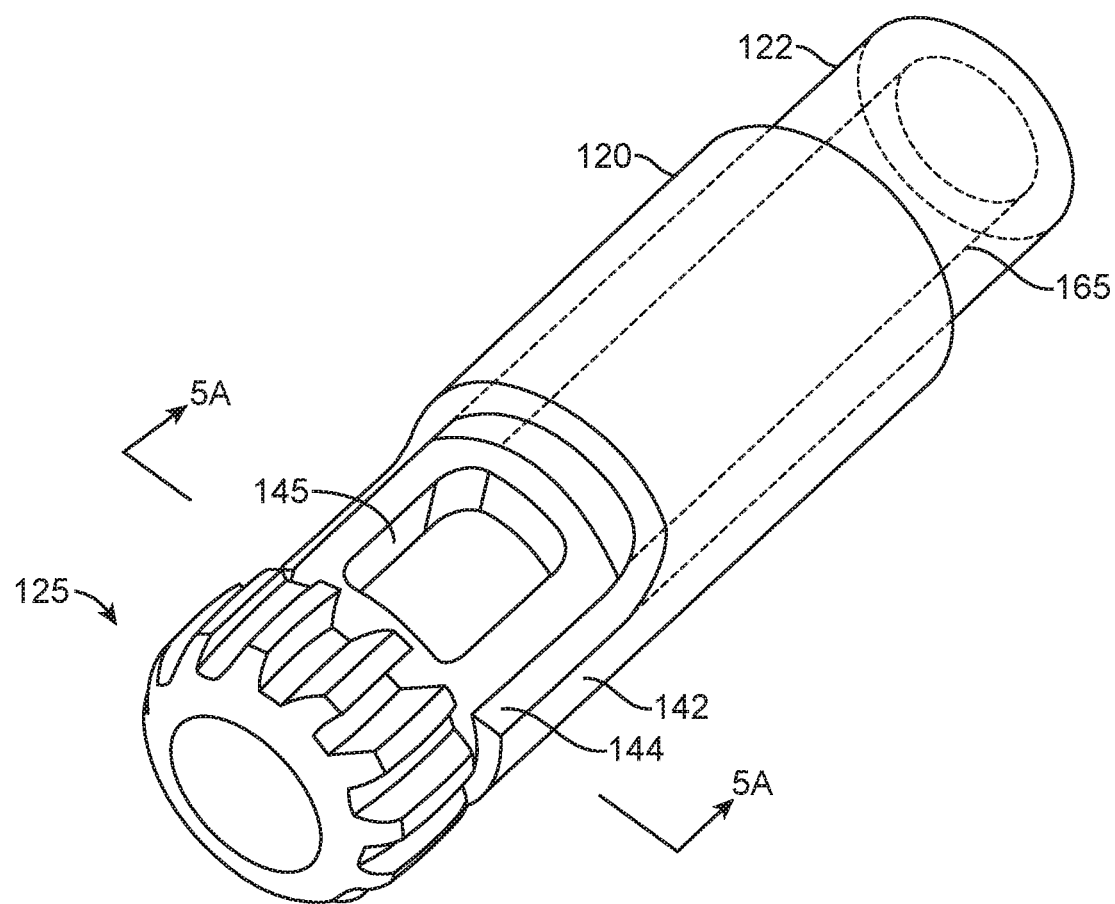
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in an manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 and 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 extending distally from the inner sleeve 122 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104 (FIG. 3). As can be seen in FIG. 1, the outer hub 140A includes a projecting key 146 that is adapted to mate with a receiving J-lock slot 148 in the handle 104 (see FIG. 3).

Figure 3:
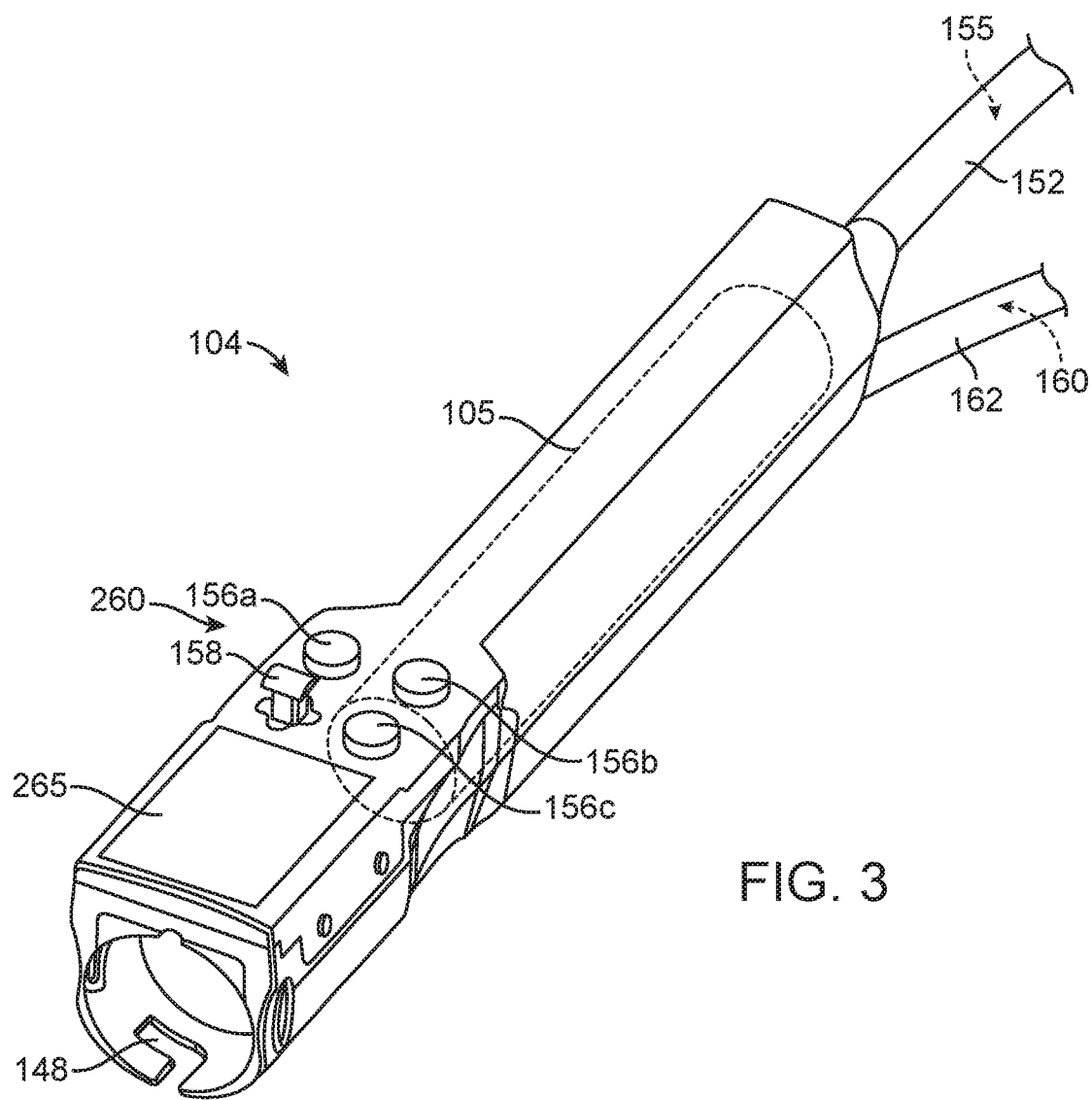
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 be moved forward and backward to adjust the rotational speed of the ceramic cutting member 125. The rotational speed of the cutter can continuously adjustable, or can be adjusted in increments up to 20,000 rpm. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
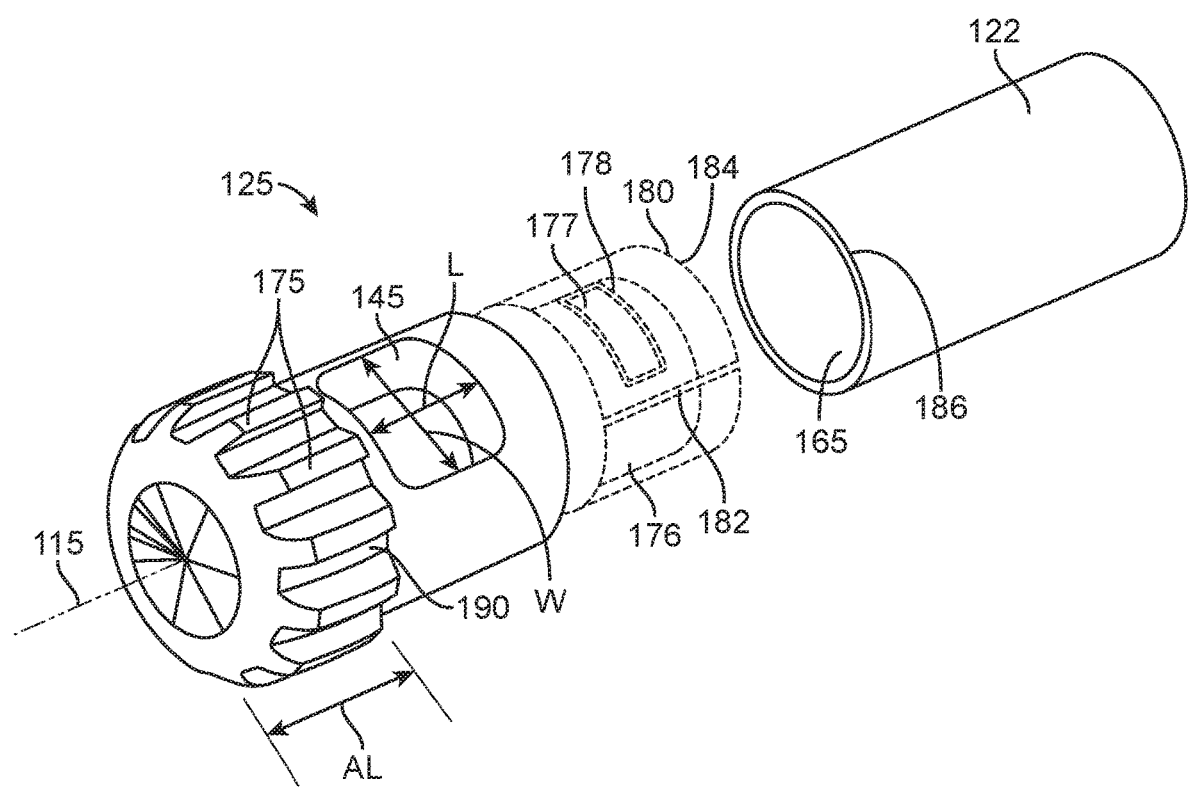
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

| | Hardness (GPa) | Fracture Toughness (MPam$^{1/2}$) | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) | | | |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) | | | |
| Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) | | | |
| YTA-14 (Superior Technical Ceramics) | 14.0 | 5 | 2.80:1 |
| ZTA (CoorsTek) | 14.8 | 6 | 2.47:1 |
| Ceria stabilized zirconia | | | |
| CSZ (Superior Technical Ceramics) | 11.7 | 12 | 0.98:1 |
| Silicon Nitride | | | |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics—Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 GPa (kg/mm$^2$). In another aspect of the invention, the ceramic cutting member 125 has a fracture toughness of at least 2 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 ($1 \times 10^6$/° C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
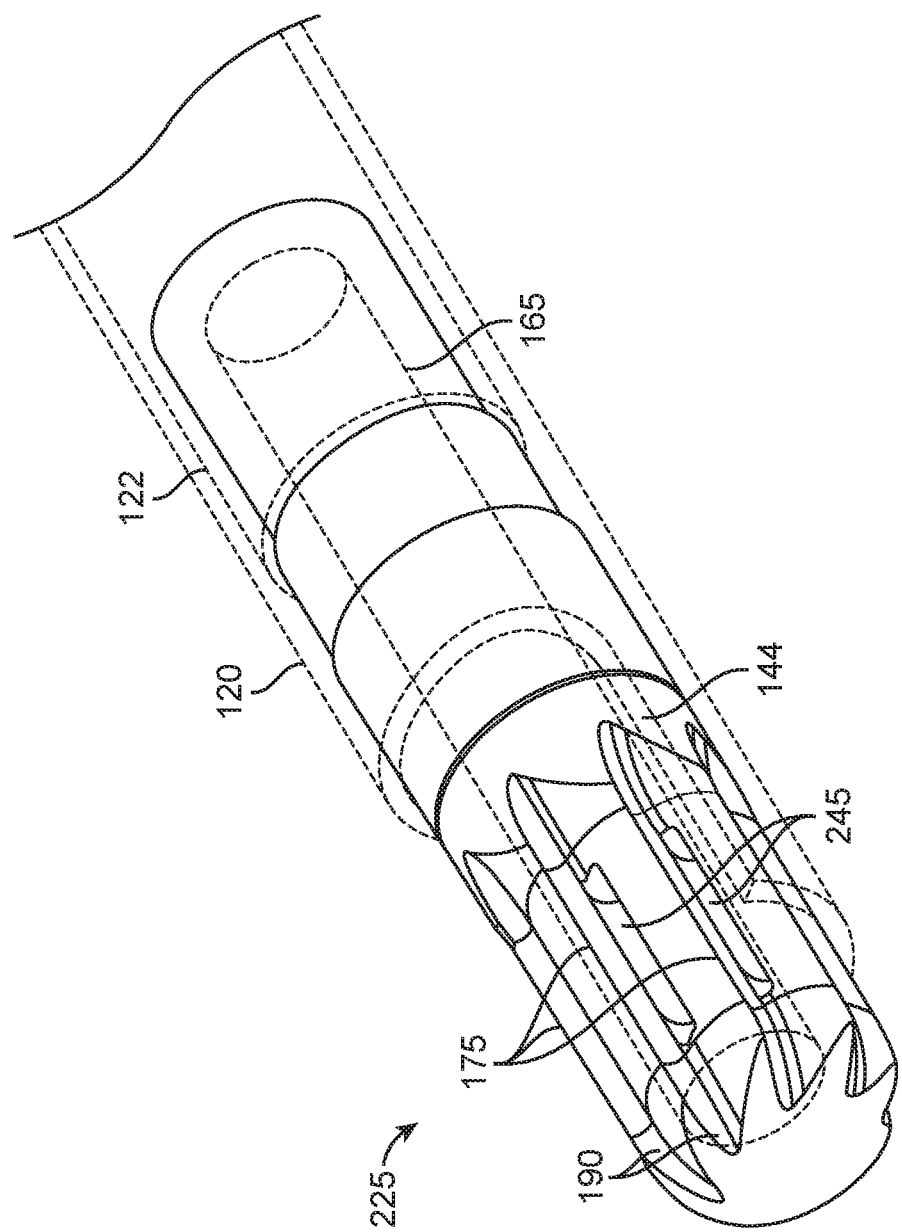
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
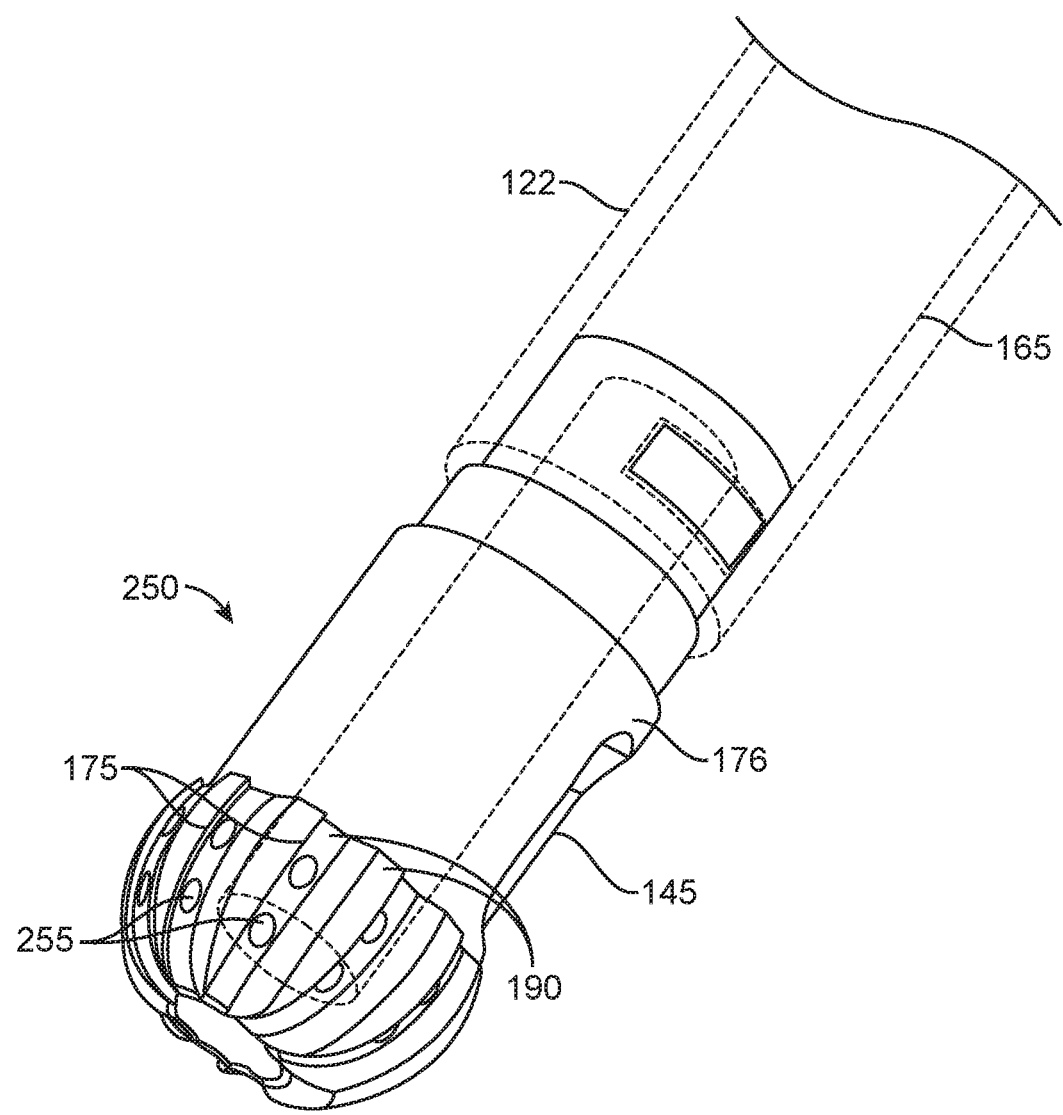
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 and intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
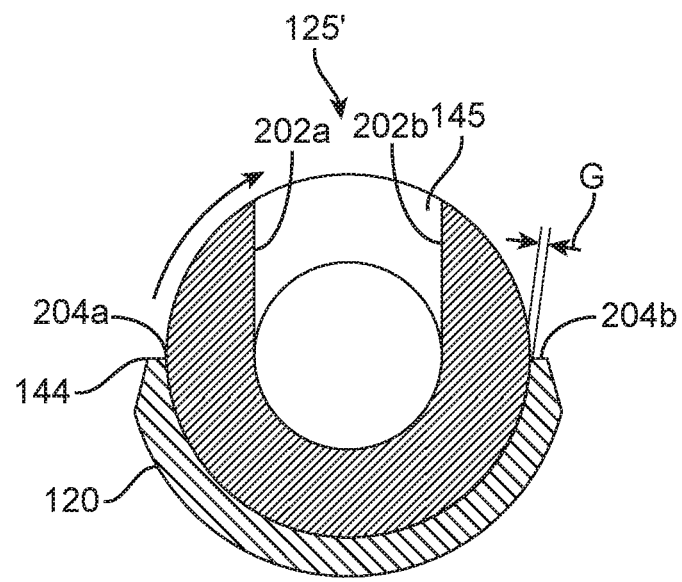
FIG. 5A is a cross-sectional view of a cutting assembly similar to that of FIG. 2 taken along line 5A-5A showing the close tolerance between sharp cutting edges of a window in a ceramic cutting member and sharp lateral edges of the outer sleeve which provides a scissor-like cutting effect in soft tissue.
Figure 5B:
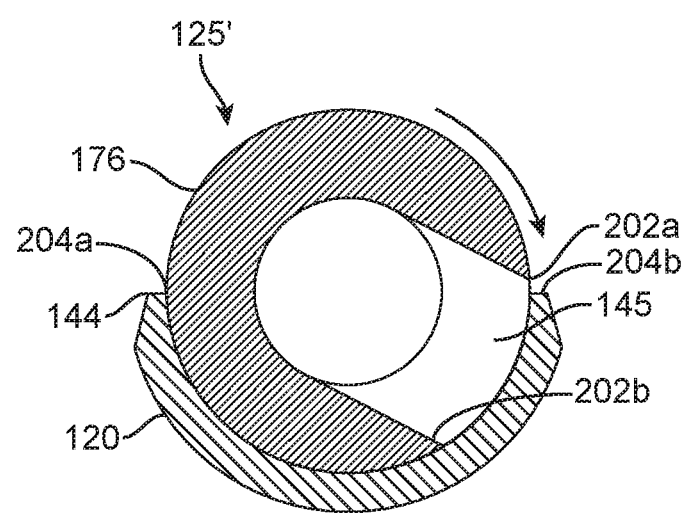
FIG. 5B is a cross-sectional view of the cutting assembly of FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020", or less than 0.010".

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 GPa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
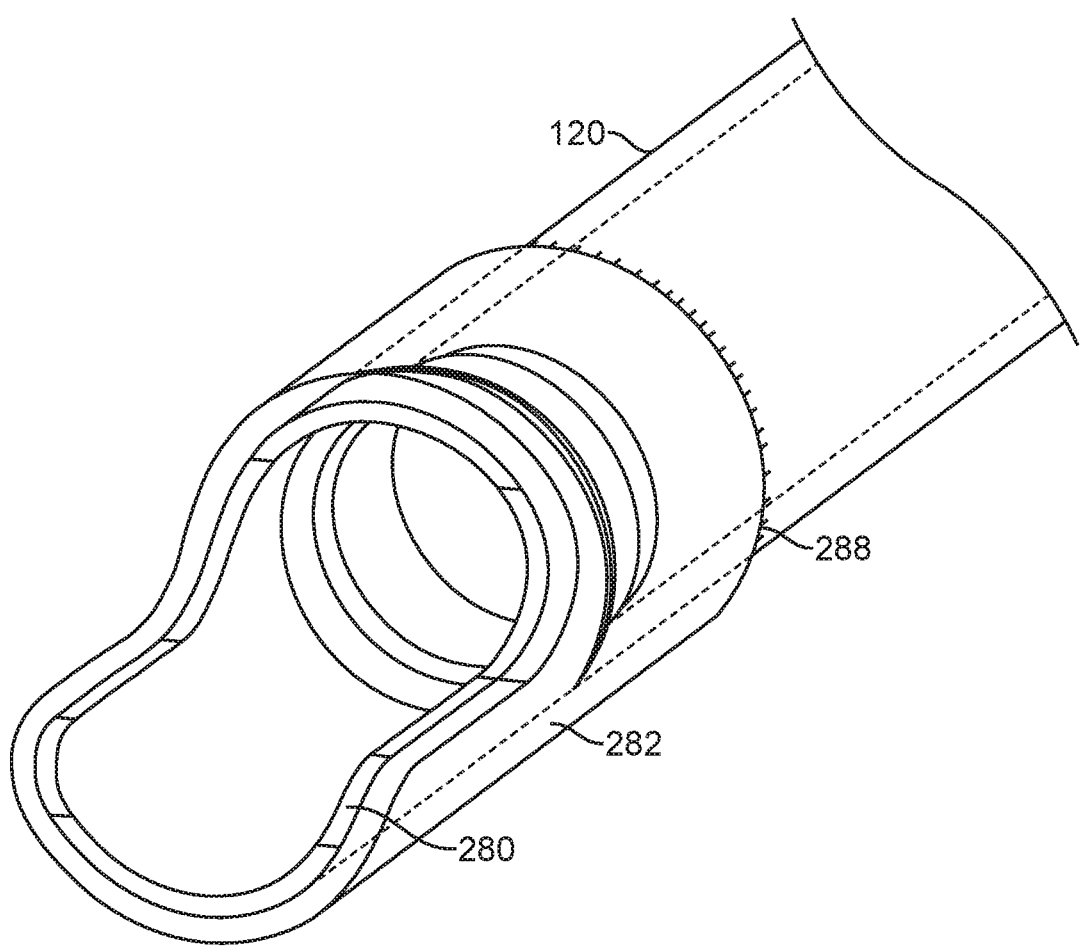
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9:
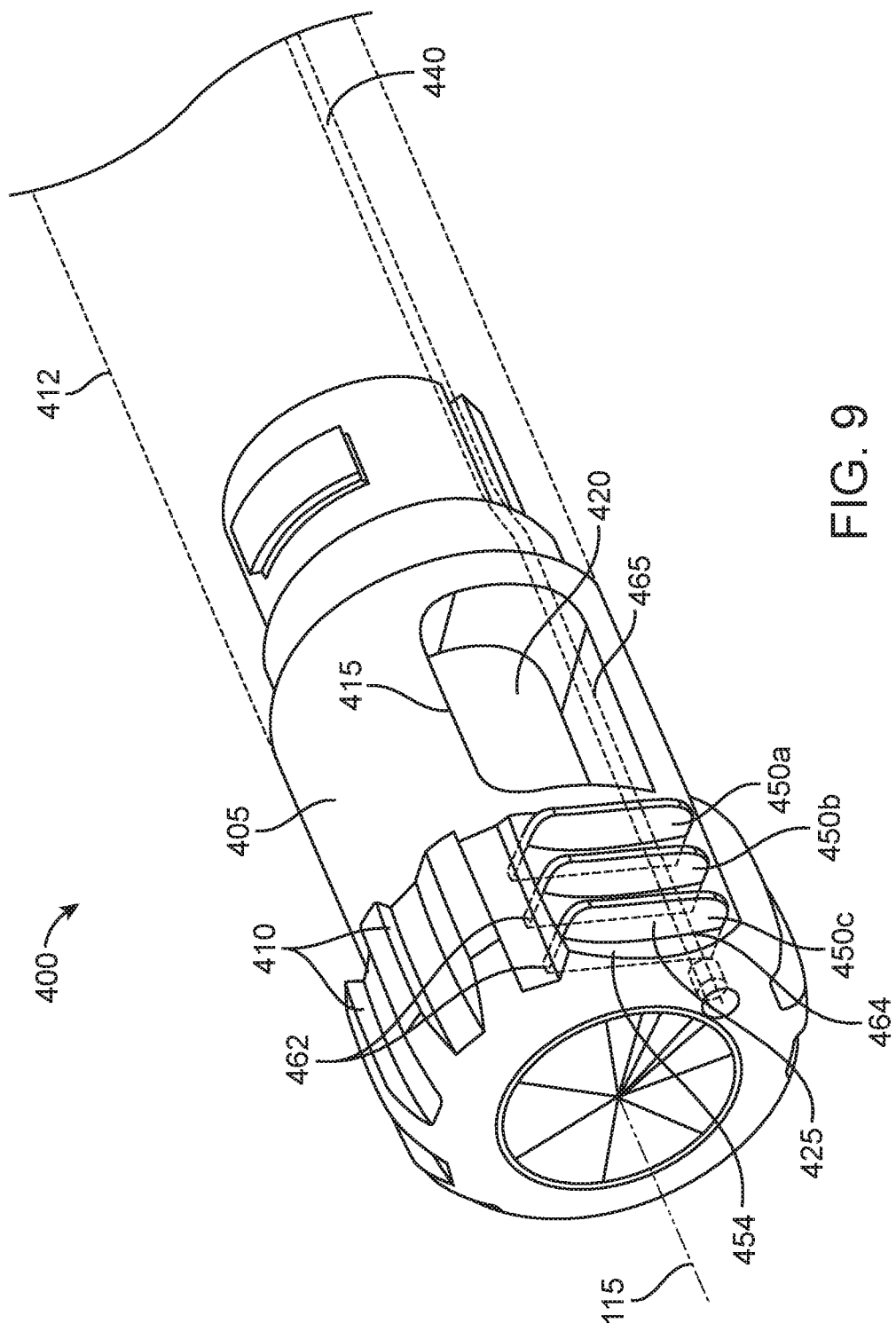
FIG. 9 is a perspective of another variation of a ceramic member with cutting edges that includes an aspiration window and an electrode arrangement positioned distal to the window.
Figure 10:
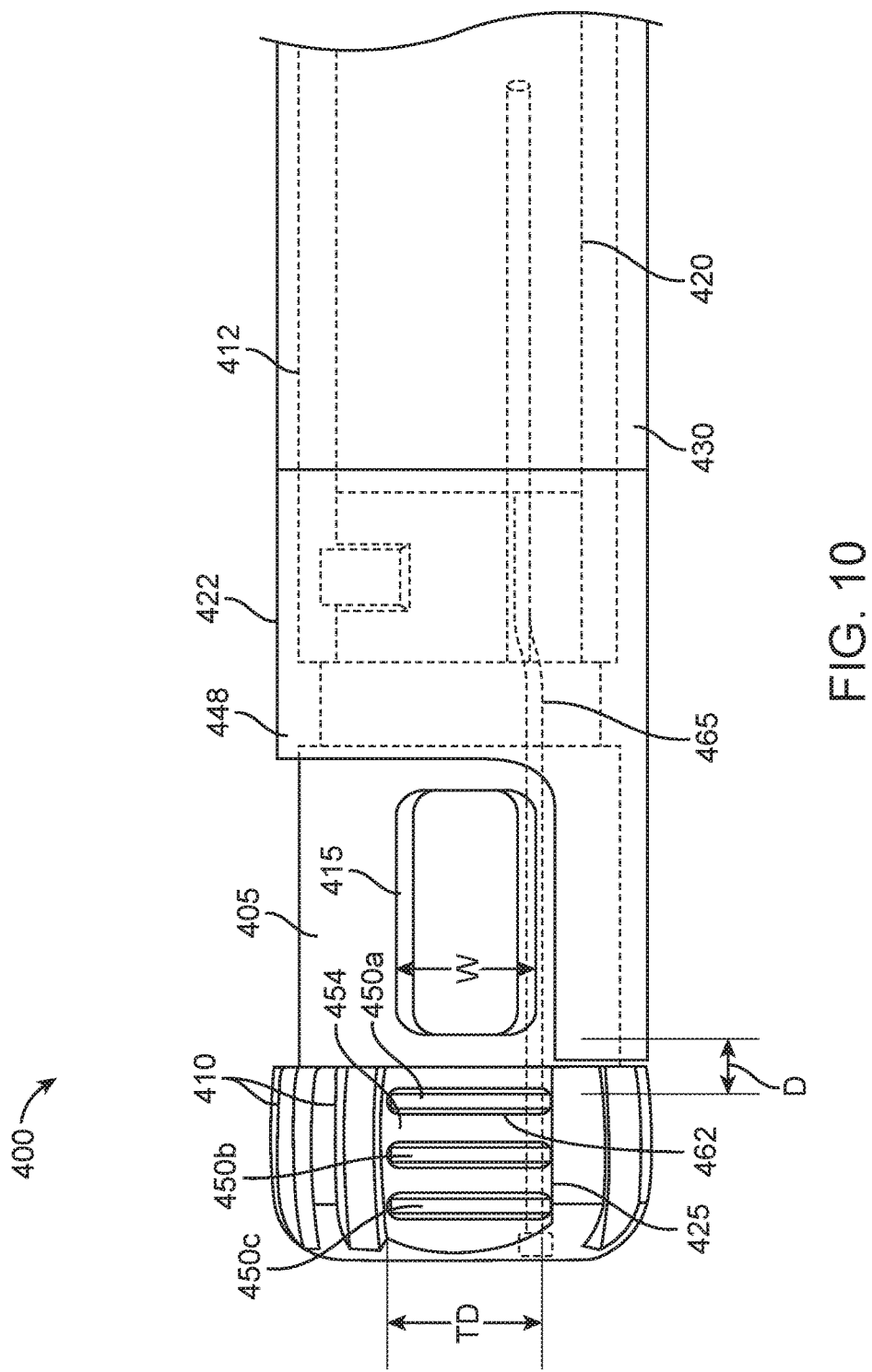
FIG. 10 is an elevational view of a ceramic member and shaft of FIG. 9 showing the width and position of the electrode arrangement in relation to the window.
Figure 11:
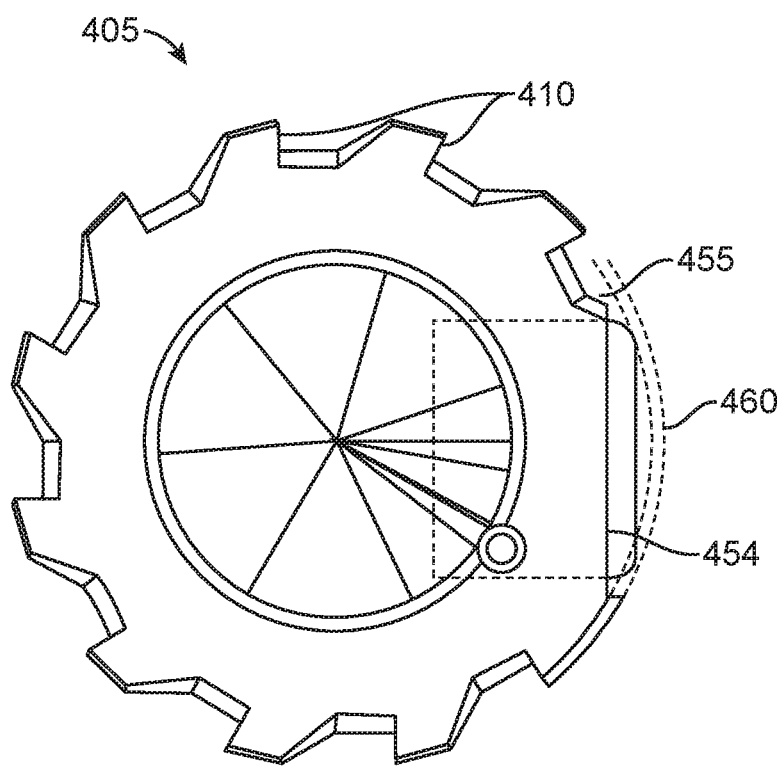
FIG. 11 is an end view of a ceramic member of FIGS. 9-10 the outward periphery of the electrode arrangement in relation to the rotational periphery of the cutting edges of the ceramic member.

FIGS. 9-11 are views of an alternative tissue resecting assembly or working end 400 that includes a ceramic member 405 (a dielectric material) with cutting edges 410 in a form similar to that described previously. FIG. 9 illustrates the monolithic ceramic member 405 carried as a distal tip of a shaft or inner sleeve 412 as described in previous embodiments. The ceramic member 405 again has a window 415 that communicates with aspiration channel 420 in shaft 412 that is connected to negative pressure source 160 as described previously. The inner sleeve 412 is operatively coupled to a motor drive 105 and rotates in an outer sleeve 422 of the type shown in FIG. 2. The outer sleeve 422 is shown in FIG. 10.

In the variation illustrated in FIG. 9, the ceramic member 405 carries an electrode arrangement 425, or active electrode, having a single polarity that is operatively connected to an RF source 440. A return electrode, or second polarity electrode 430, is provided on the outer sleeve 422 as shown in FIG. 10. In one variation, the outer sleeve 422 can comprise an electrically conductive material such as stainless steel to thereby function as return electrode 445, with a distal portion of outer sleeve 422 is optionally covered by a thin insulative layer 448 such as parylene, to space apart the active electrode 425 from the return electrode 430.

The active electrode arrangement 425 can consist of a single conductive metal element or a plurality of metal elements as shown in FIGS. 9 and 10. In one variation shown in FIG. 9, the plurality of electrode elements 450a, 450b and 450c extend transverse to the longitudinal axis 115 of ceramic member 405 and inner sleeve 412 and are slightly spaced apart in the ceramic member. In one variation shown in FIGS. 9 and 10, the active electrode 425 is spaced distance D from the distal edge 452 of window 415 which is less than 5 mm and often less than 2 mm for reasons described below. The width W and length L of window 415 can be the same as described in a previous embodiment with reference to FIG. 4.

As can be seen in FIGS. 9 and 11, the electrode arrangement 425 is carried intermediate the cutting edges 410 of the ceramic member 405 in a flattened region 454 where the cutting edges 410 have been removed. As can be best understood from FIG. 11, the outer periphery 455 of active electrode 425 is within the cylindrical or rotational periphery of the cutting edges 410 when they rotate. In FIG. 11, the rotational periphery of the cutting edges is indicated at 460. The purpose of the electrode's outer periphery 455 being equal to, or inward from, the cutting edge periphery 460 during rotation is to allow the cutting edges 410 to rotate at high RPMs to engage and cut bone or other hard tissue without the surface or the electrode 425 contacting the targeted tissue.

FIG. 9 further illustrates a method of fabricating the ceramic member 405 with the electrode arrangement 425 carried therein. The molded ceramic member 405 is fabricated with slots 462 that receive the electrode elements 450a-450c, with the electrode elements fabricated from stainless steel, tungsten or a similar conductive material. Each electrode element 450a-450c has a bore 464 extending therethrough for receiving an elongated wire electrode element 465. As can be seen in FIG. 9, and the elongated wire electrode 465 can be inserted from the distal end of the ceramic member 405 through a channel in the ceramic member 405 and through the bores 464 in the electrode elements 450a-450c. The wire electrode 465 can extend through the shaft 412 and is coupled to the RF source 440. The wire electrode element 465 thus can be used as a means of mechanically locking the electrode elements 450a-450c in slots 462 and also as a means to deliver RF energy to the electrode 425.

Another aspect of the invention is illustrated in FIGS. 9-10 wherein it can be seen that the electrode arrangement 425 has a transverse dimension TD relative to axis 115 that is substantial in comparison to the window width W as depicted in FIG. 10. In one variation, the electrode's transverse dimension TD is at least 50% of the window width W, or the transverse dimension TD is at least 80% of the window width W. In the variation of FIGS. 9-10, the electrode transverse dimension TD is 100% or more of the window width W. It has been found that tissue debris and byproducts from RF ablation are better captured and extracted by a window 415 that is wide when compared to the width of the RF plasma ablation being performed.

In general, the tissue resecting system comprises an elongated shaft with a distal tip comprising a ceramic member, a window in the ceramic member connected to an interior channel in the shaft and an electrode arrangement in the ceramic member positioned distal to the window and having a width that is at least 50% of the width W of the window, usually at least 80% of the width W of the window, and often at least 100% of the width W of the window, or greater. Further, the system includes a negative pressure source 160 in communication with the interior channel 420.

Figure 12A:
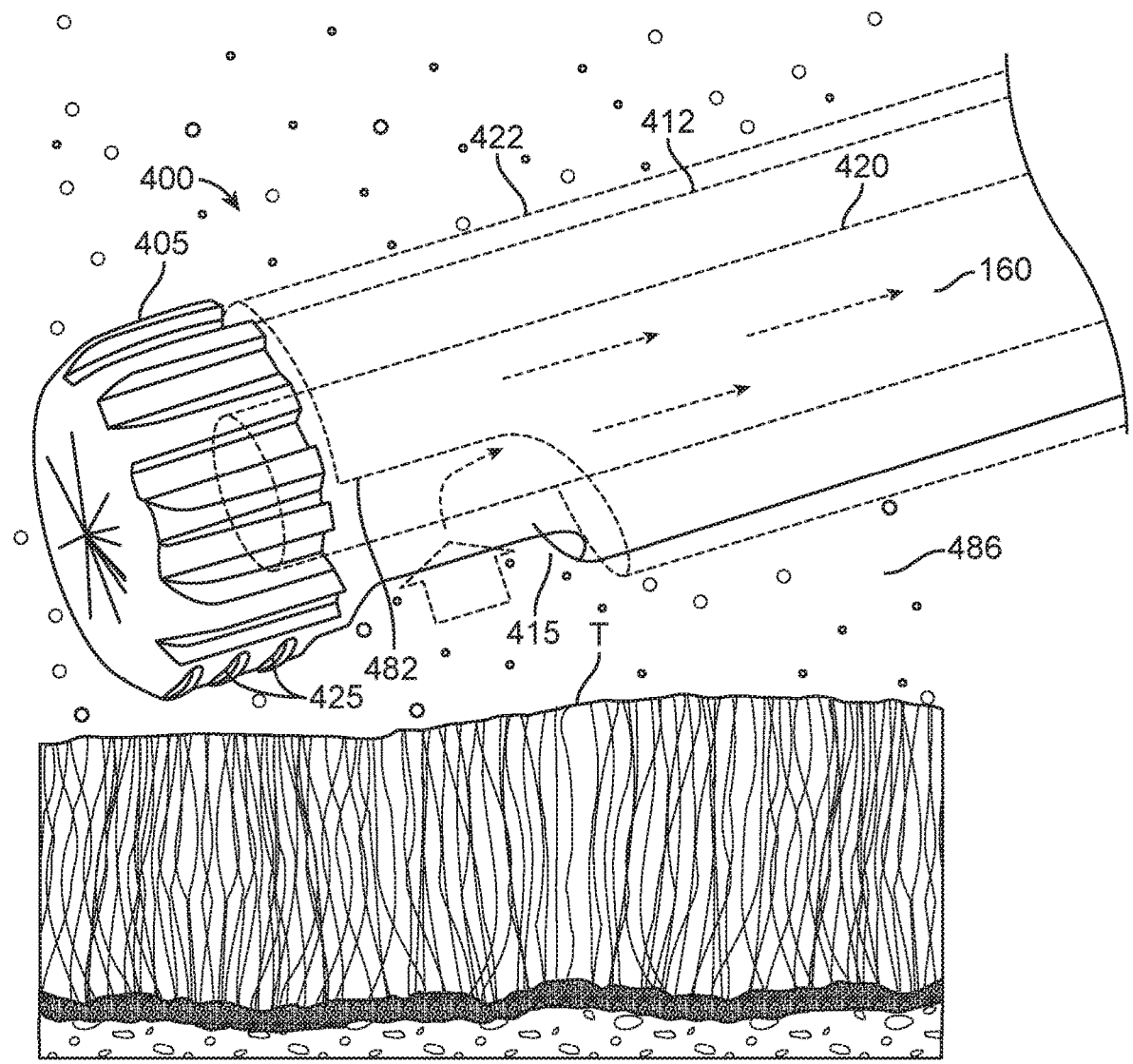
FIG. 12A is a schematic view of the working end and ceramic cutting member of FIGS. 9-11 illustrating a step in a method of use.
Figure 12B:
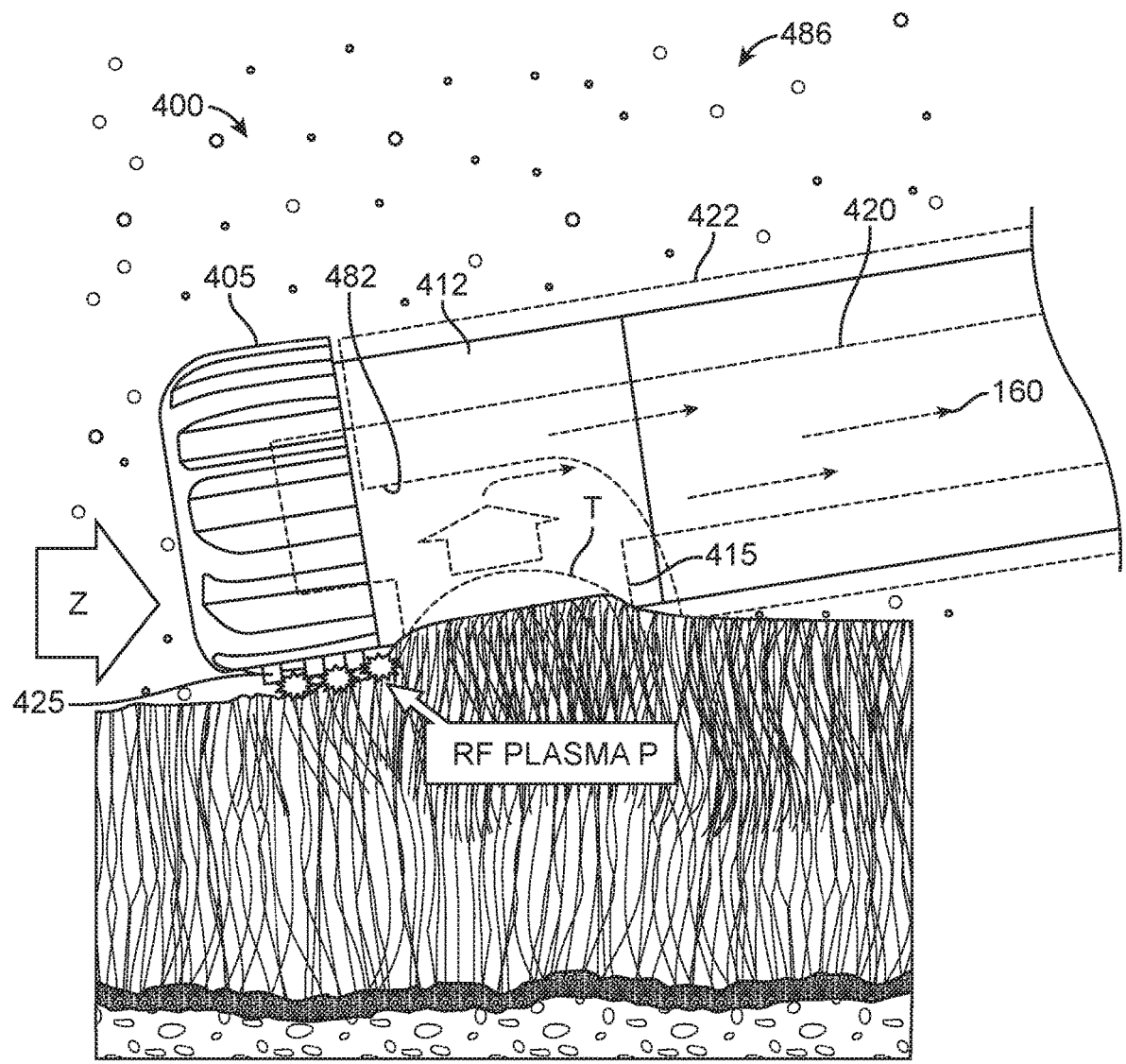
FIG. 12B is another view of the working end of FIG. 12A illustrating a subsequent step in a method of use to ablate a tissue surface.
Figure 12C:
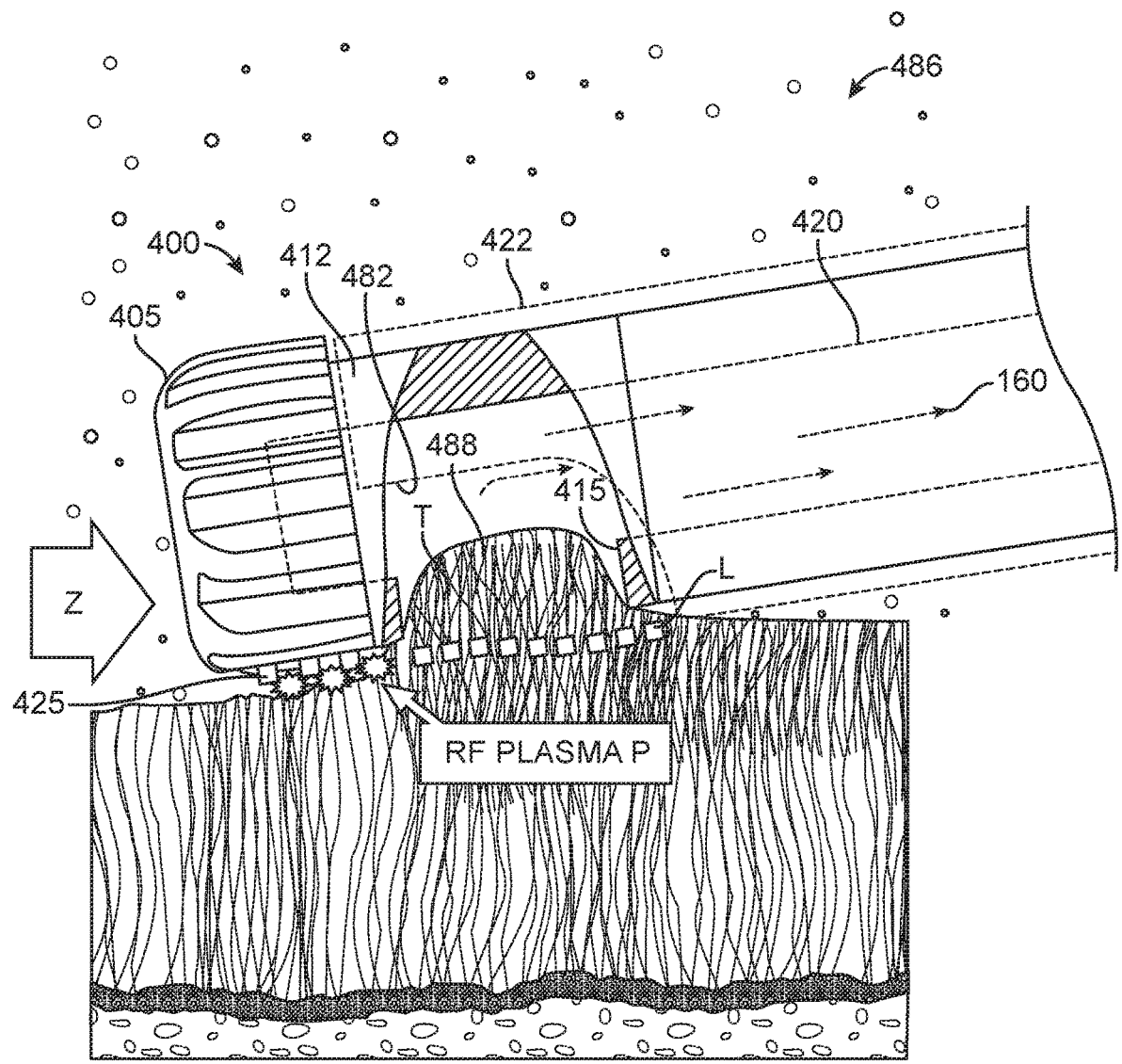
FIG. 12C is a view of the working end of FIG. 12A illustrating a method of tissue resection and aspiration of tissue chips to rapidly remove volumes of tissue.

Now turning to FIGS. 12A-12C, a method of use of the resecting assembly 400 of FIG. 9 can be explained. In FIG. 12A, the system and a controller is operated to stop rotation of the ceramic member 405 in a selected position were the window 415 is exposed in the cut-out 482 of the open end of outer sleeve 422 shown in phantom view. In one variation, a controller algorithm can be adapted to stop the rotation of the ceramic member 405 that uses a Hall sensor 484a in the handle 104 (see FIG. 3) that senses the rotation of a magnet 484b carried by inner sleeve hub 140B as shown in FIG. 2. The controller algorithm can receive signals from the Hall sensor which indicates a rotational position of the inner sleeve 412 and ceramic member 405 relative to the outer sleeve 422. The magnet 484b (FIG. 3) can be positioned in the hub 140B (FIG. 2) so that when sensed by the Hall sensor, the controller algorithm can de-activate the motor drive 105 so as to stop the rotation of the inner sleeve in any selected position, e.g. with the window 415 and cut-out 482 aligned.

Under endoscopic vision, referring to FIG. 12B, the physician then can position the electrode arrangement 425 in contact with tissue targeted T for ablation and removal in a working space filled with fluid 486, such as a saline solution which enables RF plasma creation about the electrode. The negative pressure source 160 is activated prior to or contemporaneously with the step of delivering RF energy to electrode 425. Still referring to FIG. 12B, when the ceramic member 405 is positioned in contact with tissue and translated in the direction of arrow Z, the negative pressure source 160 suctions the targeted tissue into the window 415. At the same time, RF energy delivered to electrode arrangement 425 creates a plasma P as is known in the art to thereby ablate tissue. The ablation then will be very close to the window 415 so that tissue debris, fragments, detritus and byproducts will be aspirated along with fluid 486 through the window 415 and outwardly through the interior extraction channel 420 to a collection reservoir. In one method shown schematically in FIG. 12B, a light movement or translation of electrode arrangement 425 over the targeted tissue will ablate a surface layer of the tissue and aspirate away the tissue detritus.

FIG. 12C schematically illustrates a variation of a method which is of particular interest. It has been found if suitable downward pressure on the working end 400 is provided, then axial translation of working end 400 in the direction arrow Z in FIG. 12C, together with suitable negative pressure and the RF energy delivery will cause the plasma P to undercut the targeted tissue along line L that is suctioned into window 415 and then cut and scoop out a tissue chips indicated at 488. In effect, the working end 400 then can function more as a high volume tissue resecting device instead of, or in addition to, its ability to function as a surface ablation tool. In this method, the cutting or scooping of such tissue chips 488 would allow the chips to be entrained in outflows of fluid 486 and aspirated through the extraction channel 420. It has been found that this system with an outer shaft diameter of 7.5 mm, can perform a method of the invention can ablate, resect and remove tissue at a rate greater than 15 grams/min, often greater than 20 grams/min, and sometimes greater than 25 grams/min.

In general, a method corresponding to the invention includes providing an elongated shaft with a working end 400 comprising an active electrode 425 carried adjacent to a window 415 that opens to an interior channel in the shaft which is connected to a negative pressure source, positioning the active electrode and window in contact with targeted tissue in a fluid-filled space, activating the negative pressure source to thereby suction targeted tissue into the window and delivering RF energy to the active electrode to ablate tissue while translating the working end across the targeted tissue. The method further comprises aspirating tissue debris through the interior channel 420. In a method, the working end 400 is translated to remove a surface portion of the targeted tissue. In a variation of the method, the working end 400 is translated to undercut the targeted tissue to thereby remove chips 488 of tissue.

Figure 13A:
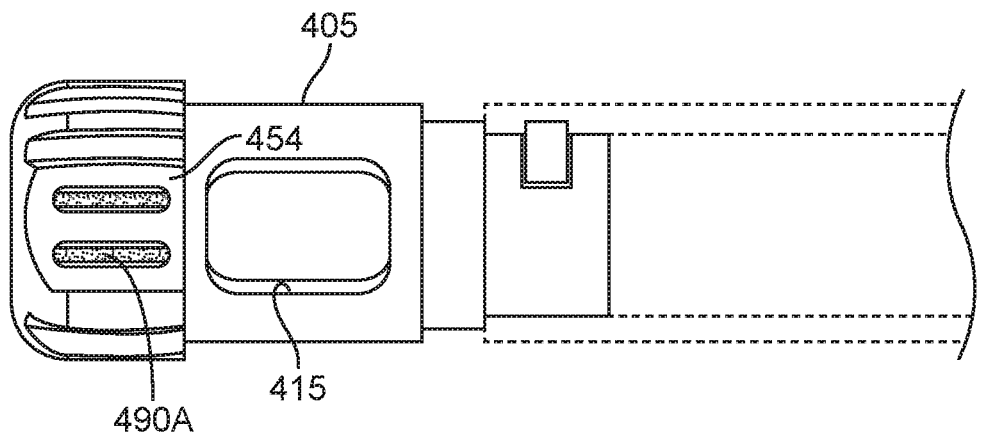
FIG. 13A is an elevational view of an alternative ceramic member and shaft similar to that of FIG. 9 illustrating an electrode variation.
Figure 13B:
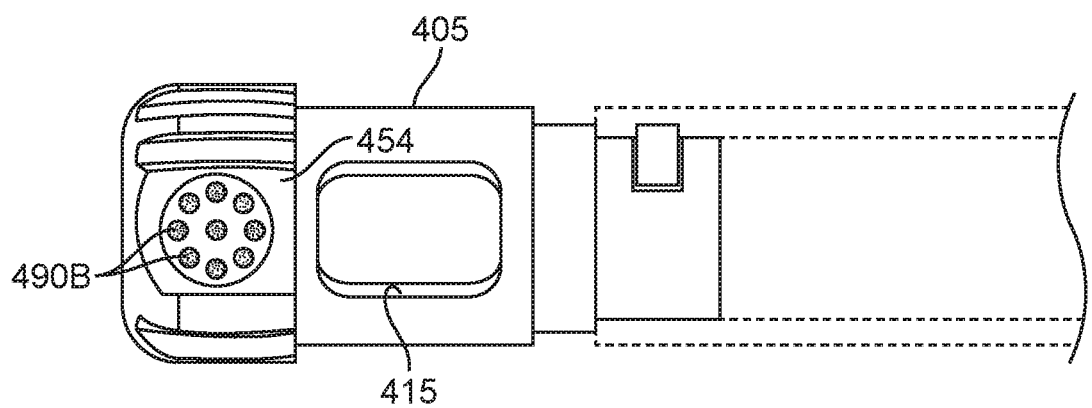
FIG. 13B is an elevational view of another ceramic member similar to that of FIG. 12A illustrating another electrode variation.
Figure 13C:
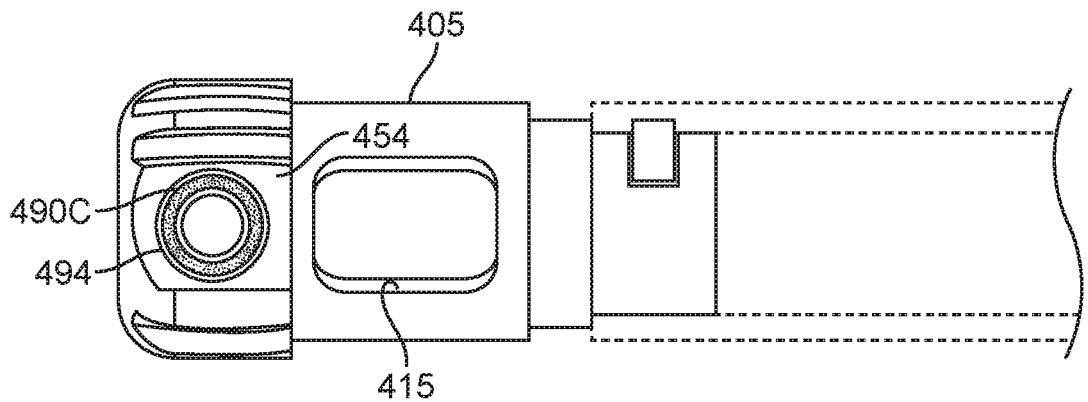
FIG. 13C is an elevational view of another ceramic member similar to that of FIGS. 12A-12B illustrating another electrode variation.

Now turning to FIGS. 13A-13C, other distal ceramic tips of cutting assemblies are illustrated that are similar to that of FIGS. 9-11, except the electrode configurations carried by the ceramic members 405 are varied. In FIG. 13A, the electrode 490A comprises one or more electrode elements extending generally axially distally from the window 415. FIG. 13B illustrates an electrode 490B that comprises a plurality of wire-like elements 492 projecting outwardly from surface 454. FIG. 13C shows electrode 490C that comprises a ring-like element that is partly recessed in a groove 494 in the ceramic body. All of these variations can produce an RF plasma that is effective for surface ablation of tissue, and are positioned adjacent to window 415 to allow aspiration of tissue detritus from the site.

Figure 14:
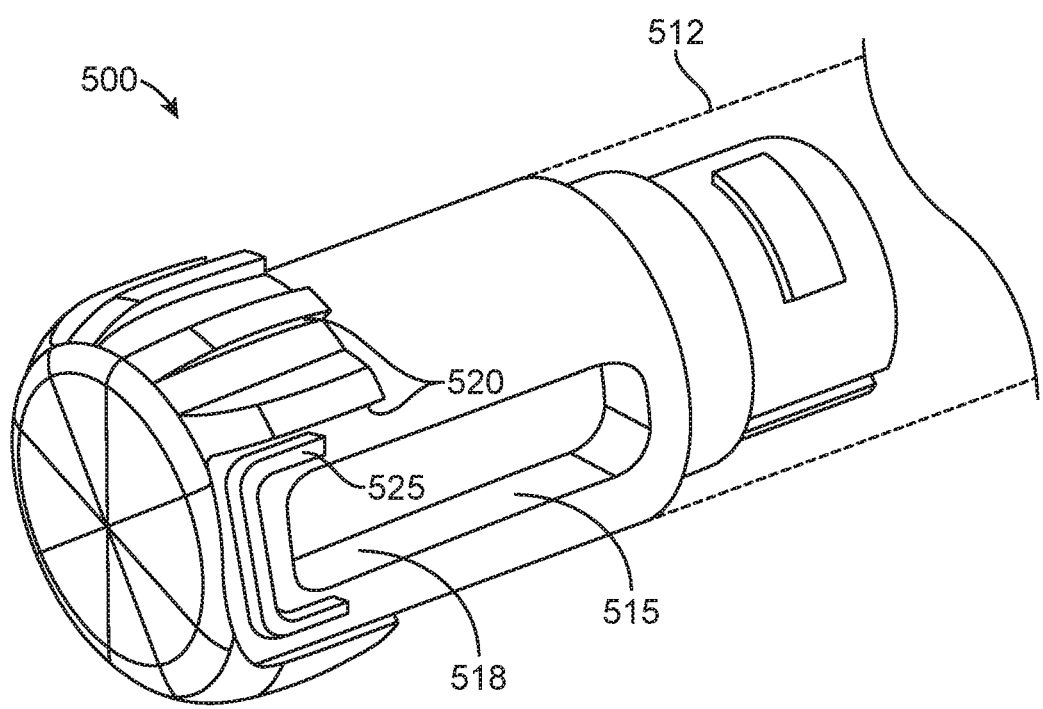
FIG. 14 is a perspective view of an alternative working end and ceramic cutting member with an electrode partly encircling a distal portion of an aspiration window.

FIG. 14 illustrates another variation of a distal ceramic tip 500 of an inner sleeve 512 that is similar to that of FIG. 9 except that the window 515 has a distal portion 518 that extends distally between the cutting edges 520, which is useful for aspirating tissue debris cut by high speed rotation of the cutting edges 520. Further, in the variation of FIG. 14, the electrode 525 encircles a distal portion 518 of window 515 which may be useful for removing tissue debris that is ablated by the electrode when the ceramic tip 500 is not rotated but translated over the targeted tissue as described above in relation to FIG. 12B. In another variation, a distal tip 500 as shown in FIG. 14 can be energized for RF ablation at the same time that the motor drive rotates back and forth (or oscillates) the ceramic member 500 in a radial arc ranging from 1° to 180° and more often from 10° to 90°.

Figure 15A:
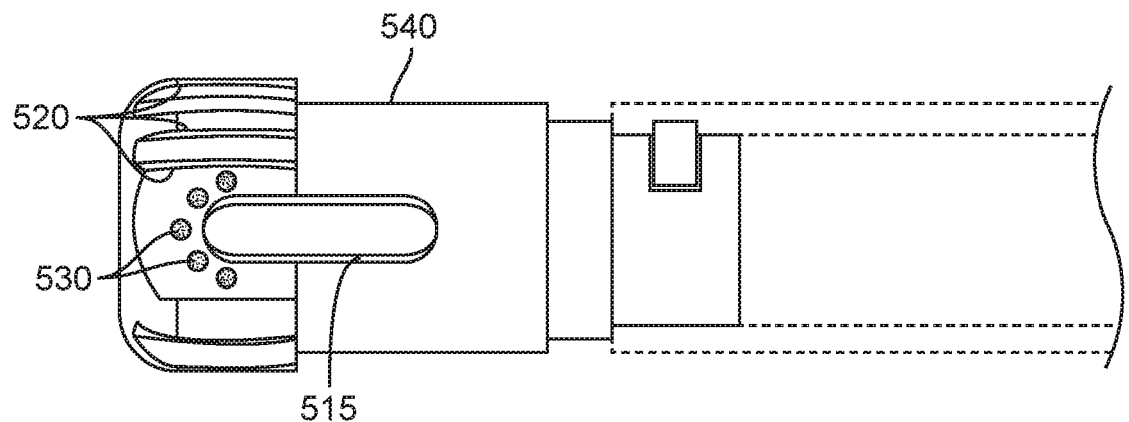
FIG. 15A is an elevational view of a working end variation with an electrode arrangement partly encircling a distal end of the aspiration window.
Figure 15B:
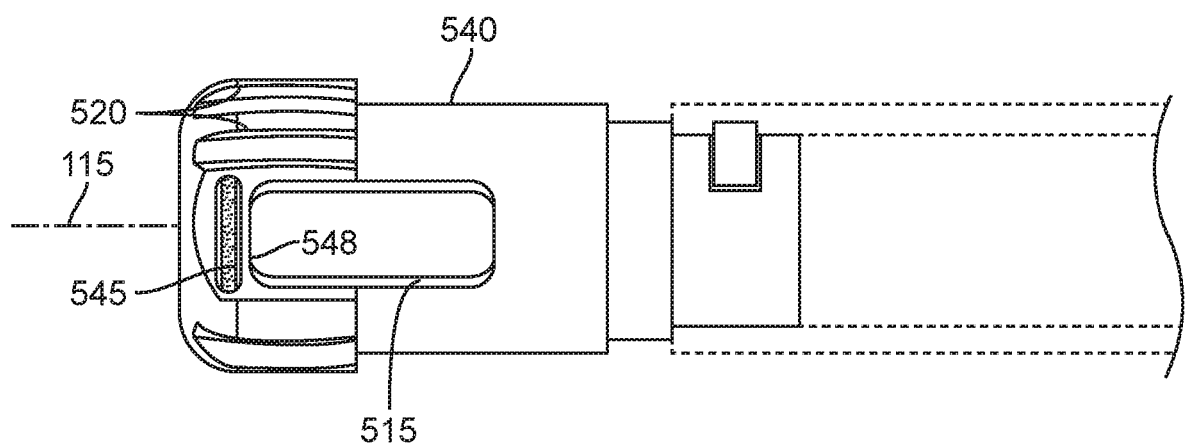
FIG. 15B is an elevational view of another working end variation with an electrode positioned adjacent a distal end of the aspiration window.

FIGS. 15A-15B illustrate other distal ceramic tips 540 and 540' that are similar to that of FIG. 14 except the electrode configurations differ. In FIG. 15A, the window 515 has a distal portion 518 that again extends distally between the cutting edges 520, with electrode 530 comprising a plurality of projecting electrode elements that extend partly around the window 515. FIG. 15B shows a ceramic tip 540' with window 515 having a distal portion 518 that again extends distally between the cutting edges 520. In this variation, the electrode 545 comprises a single blade element that extends transverse to axis 115 and is in close proximity to the distal end 548 of window 515.

Figure 16:
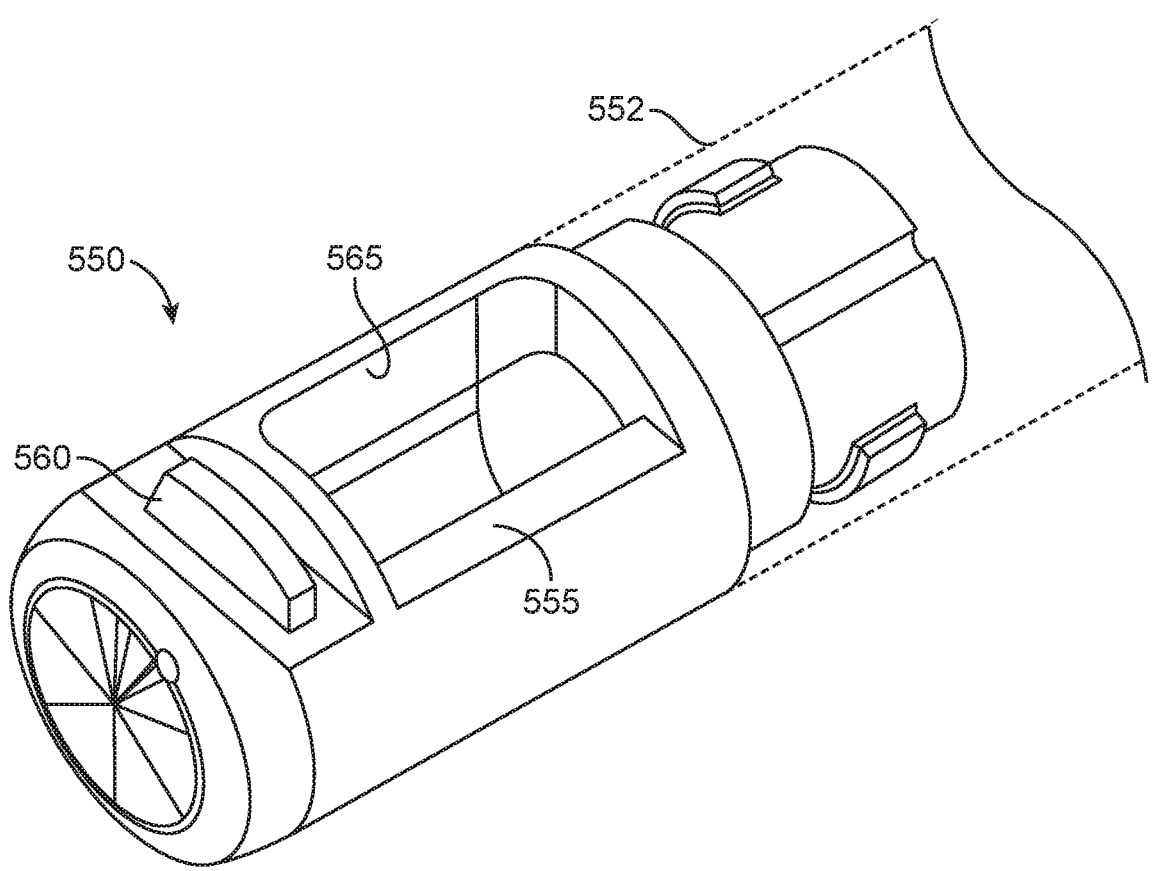
FIG. 16 is a perspective view of a variation of a working end and ceramic member with an electrode adjacent a distal end of an aspiration window having a sharp lateral edge for cutting tissue.

FIG. 16 illustrates another variation of distal ceramic tip 550 of an inner sleeve 552 that is configured without the sharp cutting edges 410 of the embodiment of FIGS. 9-11. In other respects, the arrangement of the window 555 and the electrode 560 is the same as described previously. Further, the outer periphery of the electrode is similar to the outward surface of the ceramic tip 550. In the variation of FIG. 16, the window 555 has at least one sharp edge 565 for cutting soft tissue when the assembly is rotated at a suitable speed from 500 to 5,000 rpm. When the ceramic tip member 550 is maintained in a stationary position and translated over targeted tissue, the electrode 560 can be used to ablate surface layers of tissue as described above.

Figure 17:
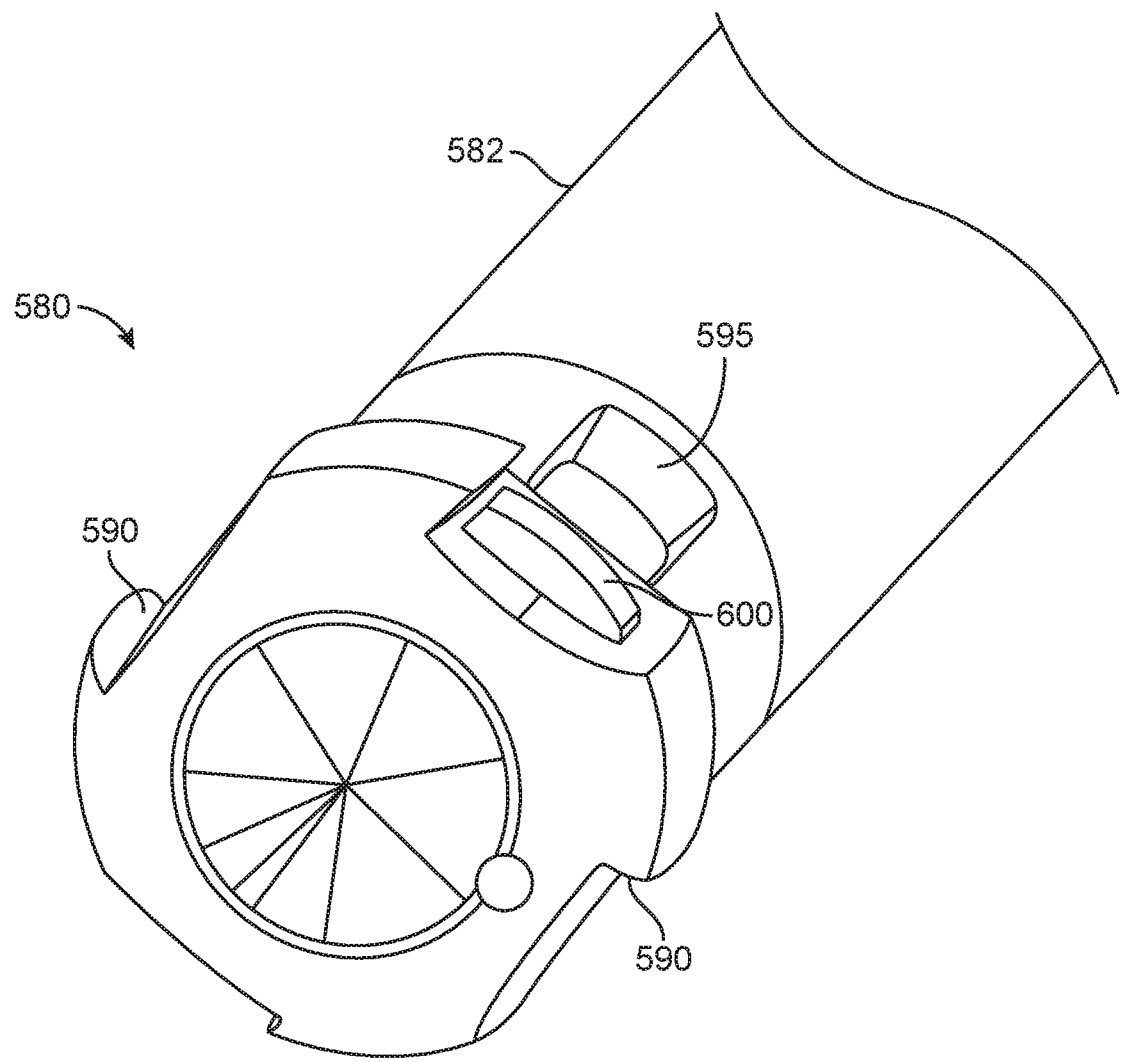
FIG. 17 is a perspective view of a variation of a working end and ceramic member with four cutting edges and an electrode adjacent a distal end of an aspiration window.

FIG. 17 depicts another variation of distal ceramic tip 580 coupled to an inner sleeve 582 that again has sharp burr edges or cutting edges 590 as in the embodiment of FIGS. 9-11. In this variation, the ceramic monolith has only 4 sharp edges 590 which has been found to work well for cutting bone at high RPMs, for example from 8,000 RPM to 20,000 RPM. In this variation, the arrangement of window 595 and electrode 600 is the same as described previously. Again, the outer periphery of electrode 595 is similar to the outward surface of the cutting edges 590.

Figure 18:
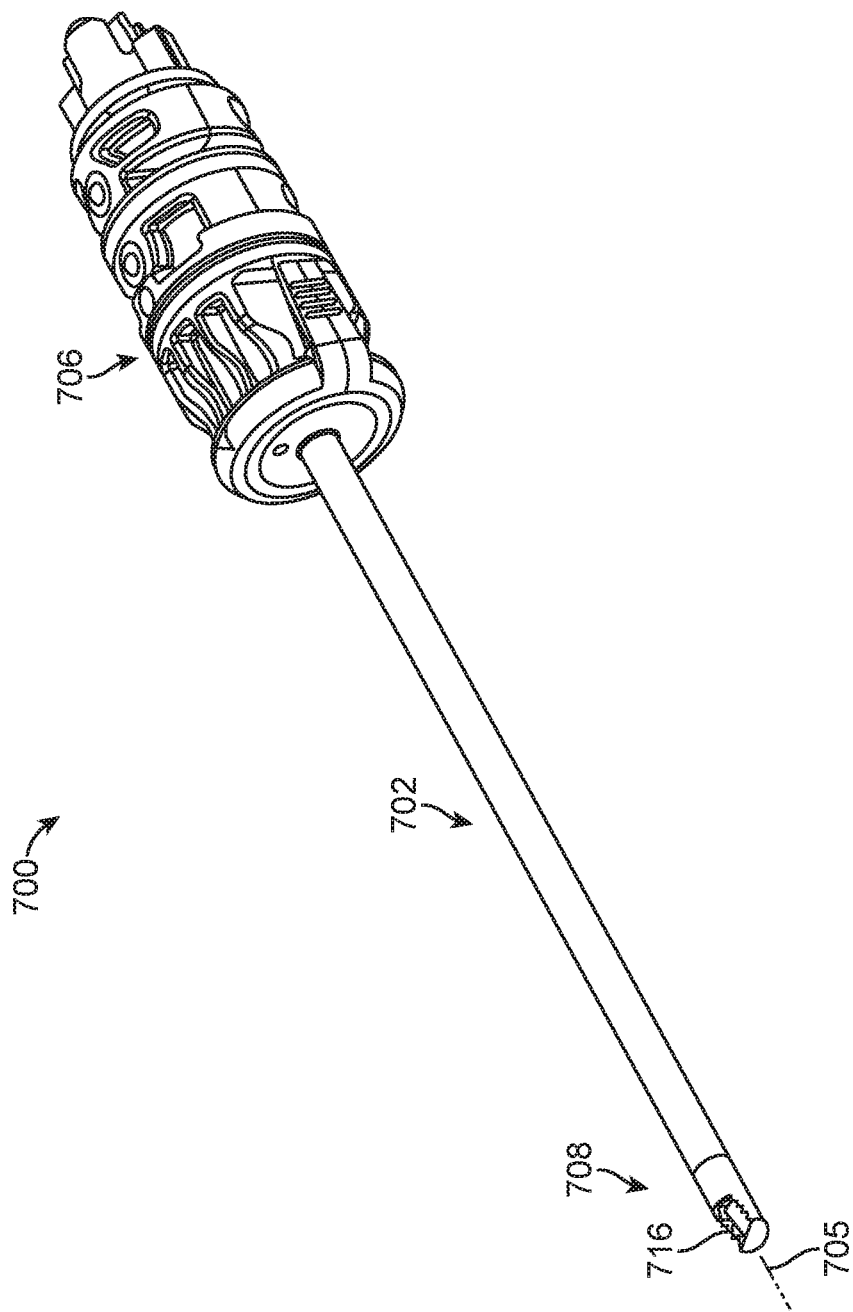
FIG. 18 is a perspective view of a variation of a shaver assembly with electrosurgical functionality.
Figure 19:
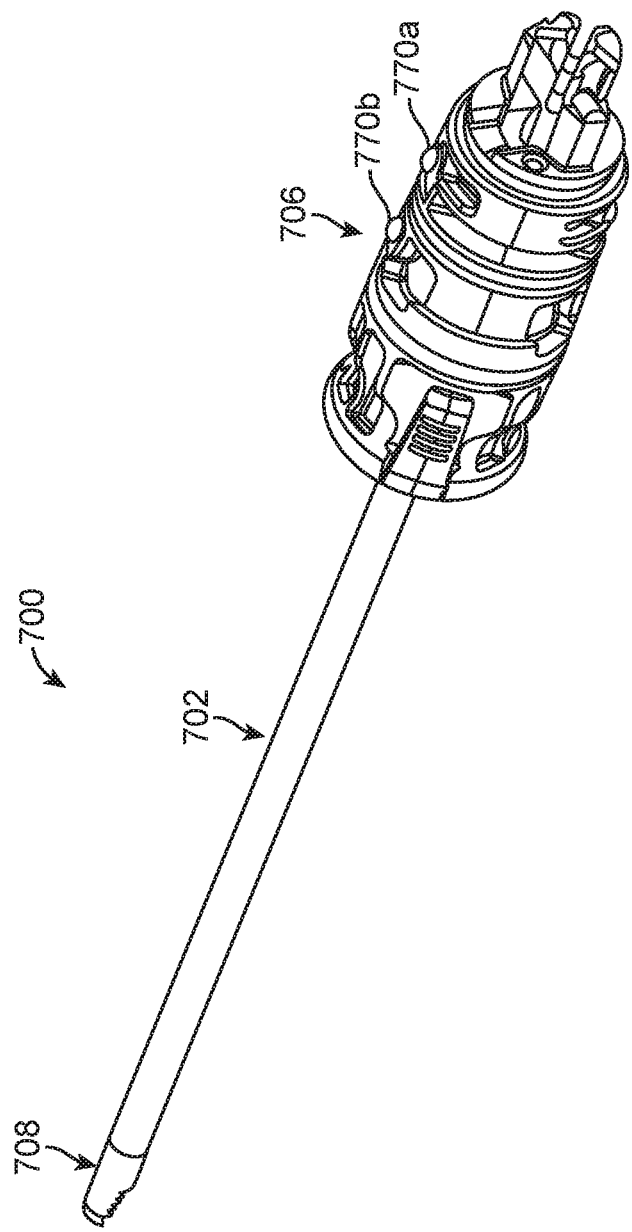
FIG. 19 is a perspective view of the shaver assembly of FIG. 18 from a different angle.

FIGS. 18 and 19 illustrate another embodiment of a shaver assembly 700. Shaver assembly 700 comprises an elongated shaft 702 extending along a longitudinal axis 705 from a proximal hub 706 that is adapted to detachably lock into a handle having a motor drive unit 105 as described previously. The shaver assembly 700 has a distal working end 708 with a windowed cutter arrangement that is similar to previous embodiments.

Figure 20:
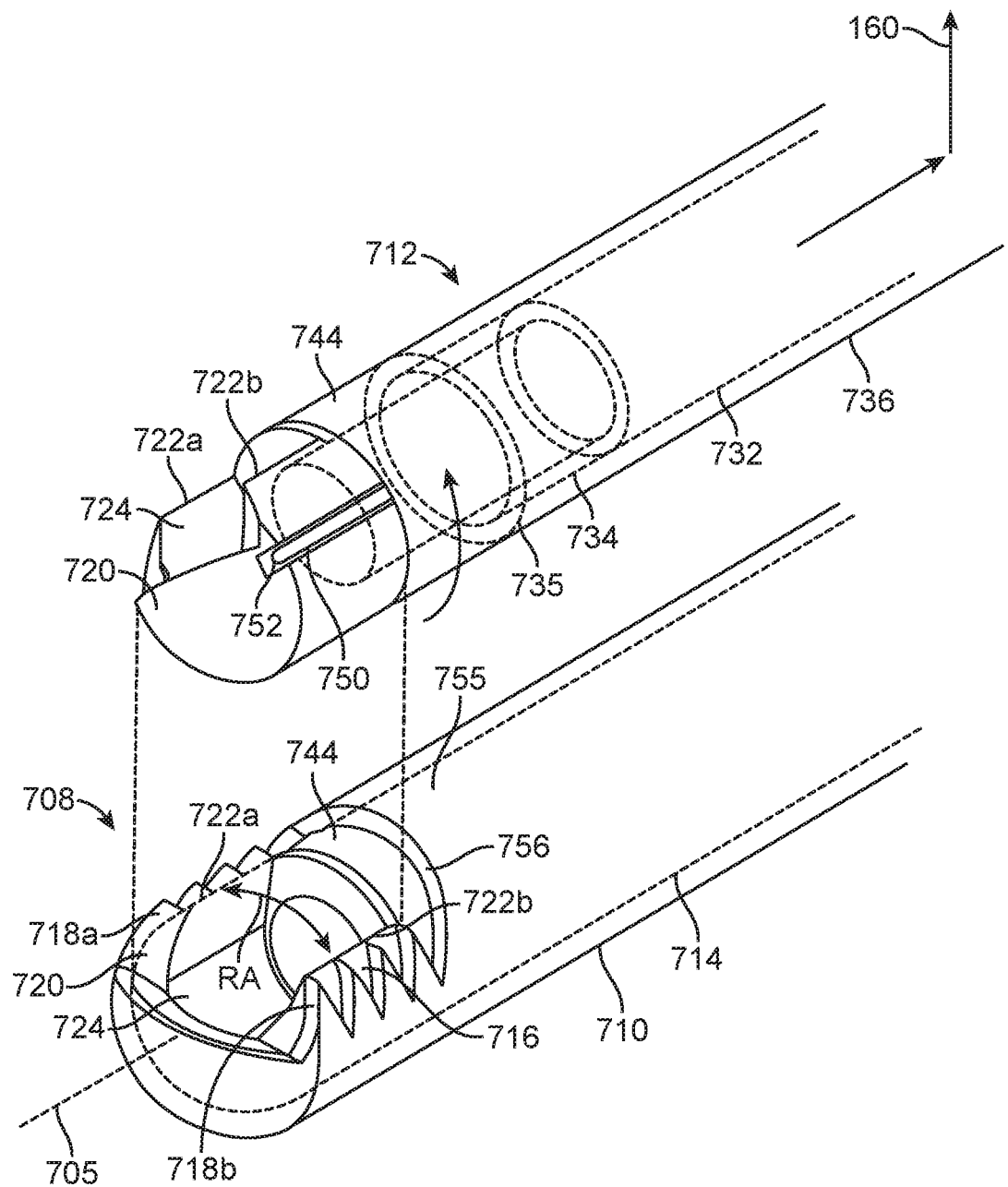
FIG. 20 is a perspective view of the working end of the shaver assembly of FIG. 18 further showing the inner sleeve separated from the outer sleeve.

FIG. 20 shows the windowed cutter arrangement of shaver assembly 700. An inner sleeve 712 is rotationally disposed in an interior bore 714 of an outer sleeve 710 in a manner similar to previous embodiments described above. The outer sleeve 710 has window 716 at its distal end with window edges 718a and 718b that can be straight, angled, sharpened, or a combination thereof. In the illustrated embodiment, the window edges 718a and 718b are serrated, having teeth as illustrated. The inner sleeve 712 a carries distal ceramic cutting member 720 that has sharp ceramic edges 722a and 722b on opposed sides of a window or opening 724 therein. The cutting member 720 can be rotated by the inner sleeve 712 so that window edges 722a and 722b on the cutter member will shear against window edges 718a and 718b on the outer sleeve 712 to mechanically cut tissue passing through window 716 in outer sleeve 710 and window 724 in the inner sleeve 712. An interior channel 732 in the inner sleeve 712 communicates with a negative pressure source 160 to aspirate cut tissue through the shaft 702 as described in previous embodiments. FIG. 20 further illustrates that the ceramic cutting member 720 has a reduced diameter proximal shaft portion 734 that extends into and interlocks with a distal end 735 of a distal portion 736 of inner sleeve 712 which can be a stainless steel hypotube.

Figure 21:
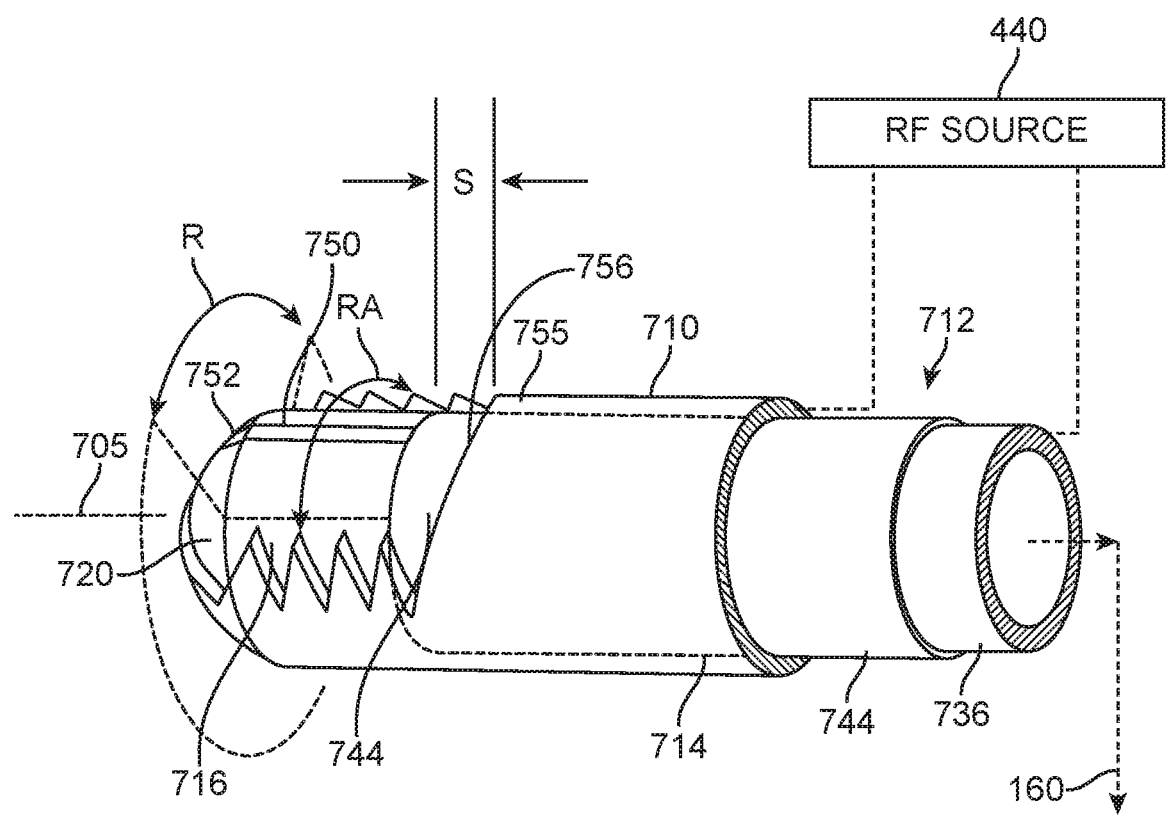
FIG. 21 is a perspective view of the working end of FIG. 20 from a different angle.

Referring further to FIG. 21, the inner sleeve 712 is typically electrically insulated, e.g. covered by an electrically insulating sleeve, layer, or coating 744 such as a shrink-wrap polymer, such as FEP. The inner sleeve 712 and cutting member 720 are coupled to a motor drive unit and controller, such as the motor drive unit 105 and the controller 155 described in FIG. 3 above, for controllably rotating the inner sleeve 712 and cutting member 720 within the outer sleeve 710.

With further reference to FIGS. 20-21, the outer sleeve 710 can comprise in part, or consist of in its entirety, a metal hypotube having an insulator layer 744 disposed over its exterior or within its interior bore 714. This allows for simplicity in manufacturing. A first or "active" electrode 750, typically in the form of a metal or other electrically conductive wire, can be carried in a channel 752 (FIG. 20) formed in the exterior surface of the ceramic cutting member 720. The active electrode 750 is electrically connected to the metal sleeve 736 of the inner sleeve 712 which is further coupled to the RF source 440 as a first electrode. The outer sleeve 710 can comprise a metal or other conductor and its exterior surface can provide a second or "return" electrode 755.

In order to provide the desired electrosurgical function, the active electrode 750 and return electrode 755 must be electrically isolated one another during operation (or the power circuit would short out). To avoid shorting, the active electrode 750 can only be powered (activated) when said active electrode 750 is exposed in window 716 of the outer sleeve 710 and thus out of contact with all portions of outer sleeve 710. Typically, the inner sleeve 712 and cutting member 720 are maintained in a stopped position where the active electrode 750 is exposed in the window 720 so that said active electrode is available to treat tissue (through window 712 in the outer sleeve 710) and remains out of contact with the return electrode 755. As can be understood from FIGS. 20 and 21, the insulator coating 744 and its positioning relative to the ceramic cutting edges 722a, 722b and the shape of the distal portion 756 of outer sleeve window 716 all cooperate to allow an "electrosurgical mode,", which can be described as a coagulation mode or ablation mode depending on the RF power and waveform selected as is known in the art.

To position the active electrode 750 and enable the electrosurgical mode, the controller 155 may be programmed or otherwise adapted to automatically stop rotation of the inner sleeve 712 and ceramic cutting member 720 in a pre-selected "stopped" rotational position around axis 705 as shown in FIG. 21. The "stopped" rotational position of cutting member 720 and electrode 750 will typically be within an angular range R which is about 10° less than the radial angle RA between the outer sleeve window edges 718a and 718b (see FIGS. 20 and 21). For example, the angular range R will usually be less than 45° within window 716, often being less than 30° within window 716. As can be best seen in FIG. 21, in the 'stopped' rotational position of cutting member 720, the distal portion 764 of insulator coating 744 is exposed in window 716 to thus provide a selected spacing S between the active electrode 750 and the return electrode 755. The spacing S can be at least 1 mm, and more often at least 2 mm. FIGS. 20-21 further illustrate that the insulator coating 744 can extend distally to be even with or very close to the proximal end 772 of the ceramic cutting edges 722a and 722b. Further, the proximal end 756 of window 716 is angled or slanted proximally toward its outer periphery. These features and characteristics cooperate to provide a spacing S between the active and return electrodes 750, 755 as shown in FIG. 21.

In another variation, the controller 155 can be programmed or adapted to provide a plurality of "stopped" positions which can provide for open gaps having different widths to control suction through the partly aligned windows 716 and 725, or the windows may be moved completely out of alignment (closed) to stop suction and prevent any loss of material which had been previously aspirated. Further, the controller 155 can be adapted to modulate, pulse, or terminate fluid outflows through partly aligned windows 716 and 725 while operating in the electrosurgical mode to optimize RF coagulation or RF ablation parameters.

In specific examples, the controller 155 and motor drive unit 105 are configured with a sensor or other mechanism to automatically stop rotation of the inner sleeve 712 within the outer sleeve 710 with the electrode 750 exposed generally in the center of window 716. A number of mechanisms can be used for stopping rotation of the inner sleeve 712 in a known location. For example, Hall sensors or micro-switches in the inner and outer hubs (see FIG. 1 and accompanying text) can provide signals to the controller 155 that indicate the rotational position of the inner sleeve 712 each time the inner sleeve rotates in 360°. The controller 155 can then control voltage to the motor drive unit 105 and/or brake the speed of rotation to cause the inner sleeve 712 to stop rotation in the pre-selected position.

FIG. 21 further schematically shows an RF source 440 coupled to the outer sleeve 710 and inner sleeve 712. As can be seen in FIG. 19, electrical contacts 770a and 770b in hub 760 connect to cooperating contacts in handle 104 to couple electrical power to the shaver assembly.

Figure 22:
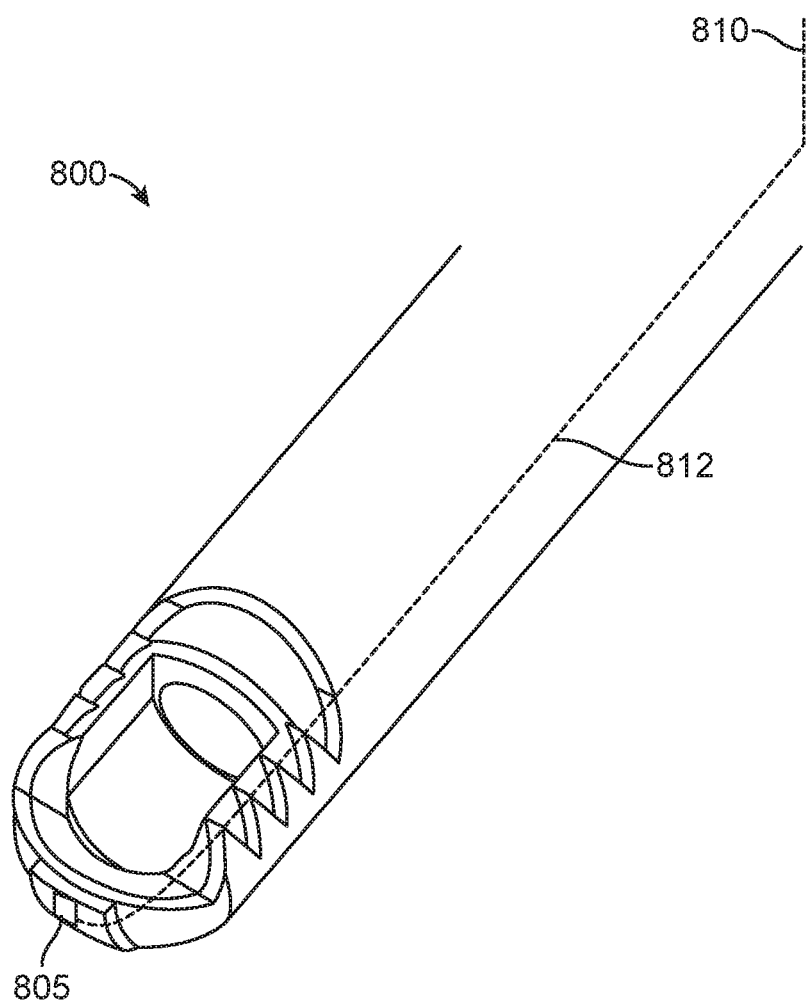
FIG. 22 is a perspective view of another variation of working end of a shaver assembly that carries a light emitter.
Figure 23:
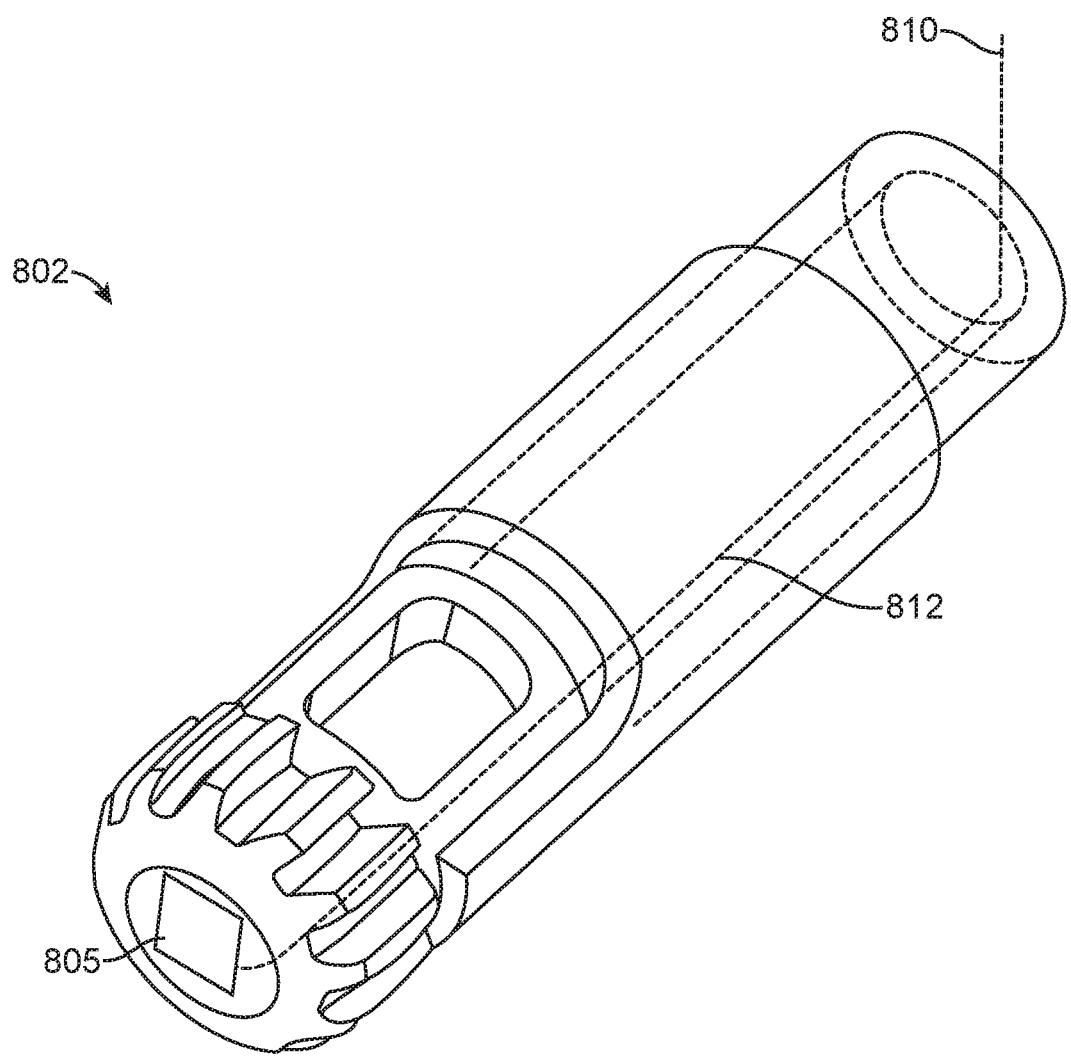
FIG. 23 is a perspective view of another working end of a burr and shaver device that carries a light emitter.

In another aspect of the invention, FIGS. 22 and 23 illustrate shaver assemblies 800 and 802 that are similar to previous embodiments in cutting and electrosurgical functionality. In these variations, the distal ends 802 of the shaver assemblies each carry a light emitter 805. In one variation the light emitter can be a light emitting diode (LED) which is connected to a power source 810 through electrical lead 812. The light emitter 805 can be located in or on a surface of a distal tip of an outer sleeve (FIG. 22) or can be located in or on a surface of a distal tip of a cutter and inner sleeve assembly (FIG. 23), e.g. on the distal tip of the ceramic cutting member. It can be understood that in many procedures in which cutting is done, the physician may rely on the translucent characteristics of tissue to determine the thickness of anatomic structures, the cutting depth, the location of adjacent anatomic structures and the like. In current practice, the lighting would come from the distal end of an endoscope in the working space which may or may not be optimal. In this variation, the tip of the cutting instrument itself would carry the light emitter and the viewing could be through the endoscope with its light source turned off, or optionally turned on at a selected power level. It is believed that in many procedures, such a light emitter 805 adjacent to, or beyond, the tip of the cutting member will provide important visual clues as to the cutting process. For example in ENT procedures, cutting tissues in a nasal passageway may be assisted greatly by a by a light emitter at the tip of the cutting assembly.

Now turning to FIGS. 24A-26, another variation of a shaver working end 900 of a cutting device or probe is shown, which is similar to the embodiment described with reference to FIGS. 18-21. In this variation, a ceramic body 905 again extends along axis 906 from the distal end 908 of inner sleeve 910 (see FIGS. 24B, 25B). The inner sleeve 910 rotates in bore 912 of outer sleeve 915 which has a distal end 916 with a window or cut-out opening 920 that again is similar to previous embodiments. The inner sleeve 910 and the outer sleeve 915 again can be metal hypotubes and can range in diameter from 3 mm to 8 mm or more.

Figure 24A:
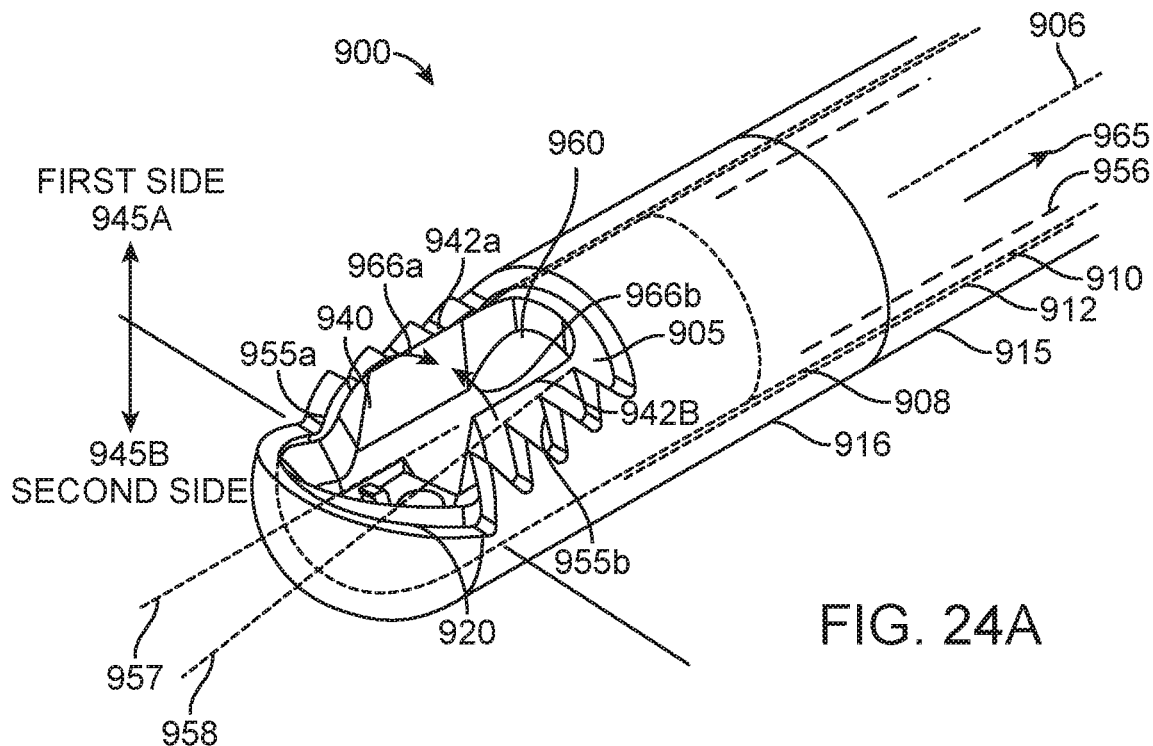
FIG. 24A is a perspective view of a working end of another tissue removal device or shaver that carries an electrode arrangement for ablating or coagulating tissue, with cutting edges of a ceramic windowed cutting member in a first position.
Figure 24B:
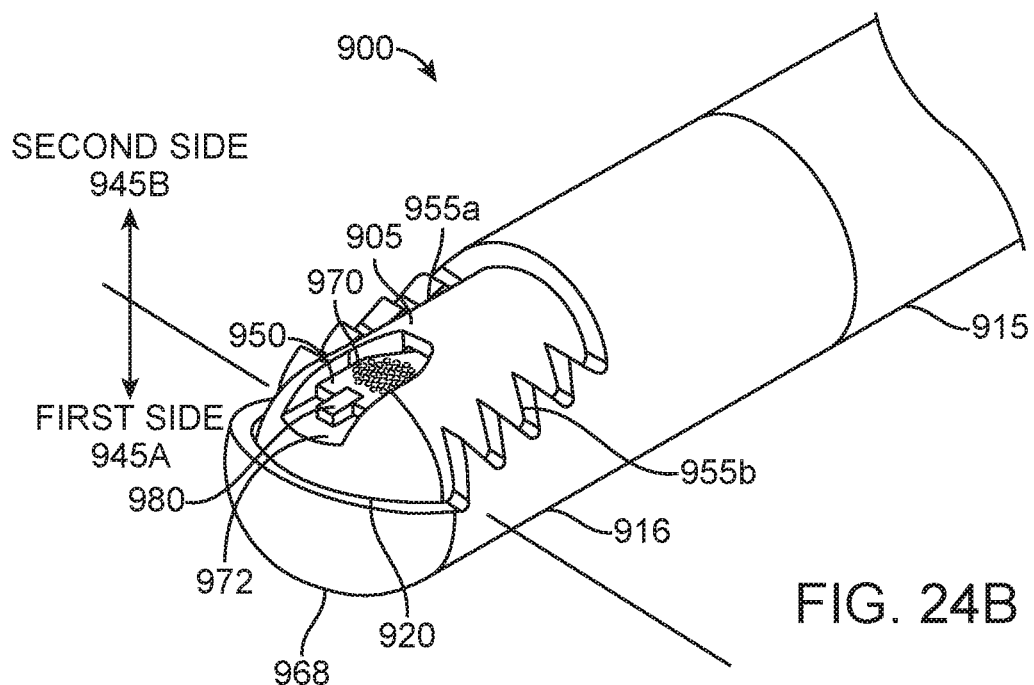
FIG. 24B is another perspective view of the working end of FIG. 24A with the inner ceramic cutting member in a second position.

As can be seen from FIGS. 24A and 24B, the ceramic body or cutting member 905 differs from the previous embodiment in that cutting member window 940 with cutting edges 942A and 942B is disposed in a first side 945A of ceramic body 905 and the electrode 950 is disposed on a second side 945B of the ceramic body. From FIG. 24A, it can be understood that cutting window 940 rotates within the cut-out opening or window 920 of outer sleeve 915 so that tissue is cut in a scissor-like manner as the cutting edges 942A and 942B shear past the cut-out edges or outer window edges 955A and 955B as described previously. The cut-out edges 955A and 955B may be linear or have teeth as shown in FIGS. 24A-24B. In one variation shown in FIG. 24A, the ceramic cutting member's cutting edges 942A and 942B extend longitudinally in parallel with the assembly longitudinal axis 906 indicated by line 957 while the outer sleeve's cut-out edges 955A and 955B are angled as indicated by line 958. During rotation of the cutting member at high speed, the shearing action will cut tissue more like a scissor with one cutting edge crossing the other progressively which can lead to smoother cutting.

Figure 25A:
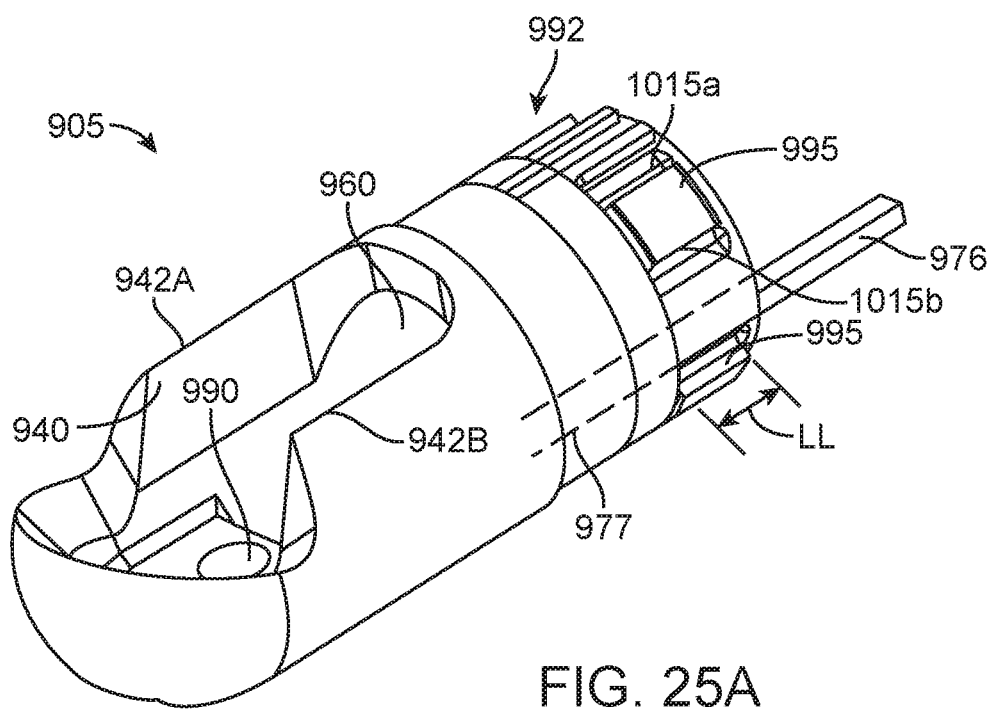
FIG. 25A is a perspective view of a first side of the ceramic cutting member of FIG. 24A without the outer sleeve.
Figure 25B:
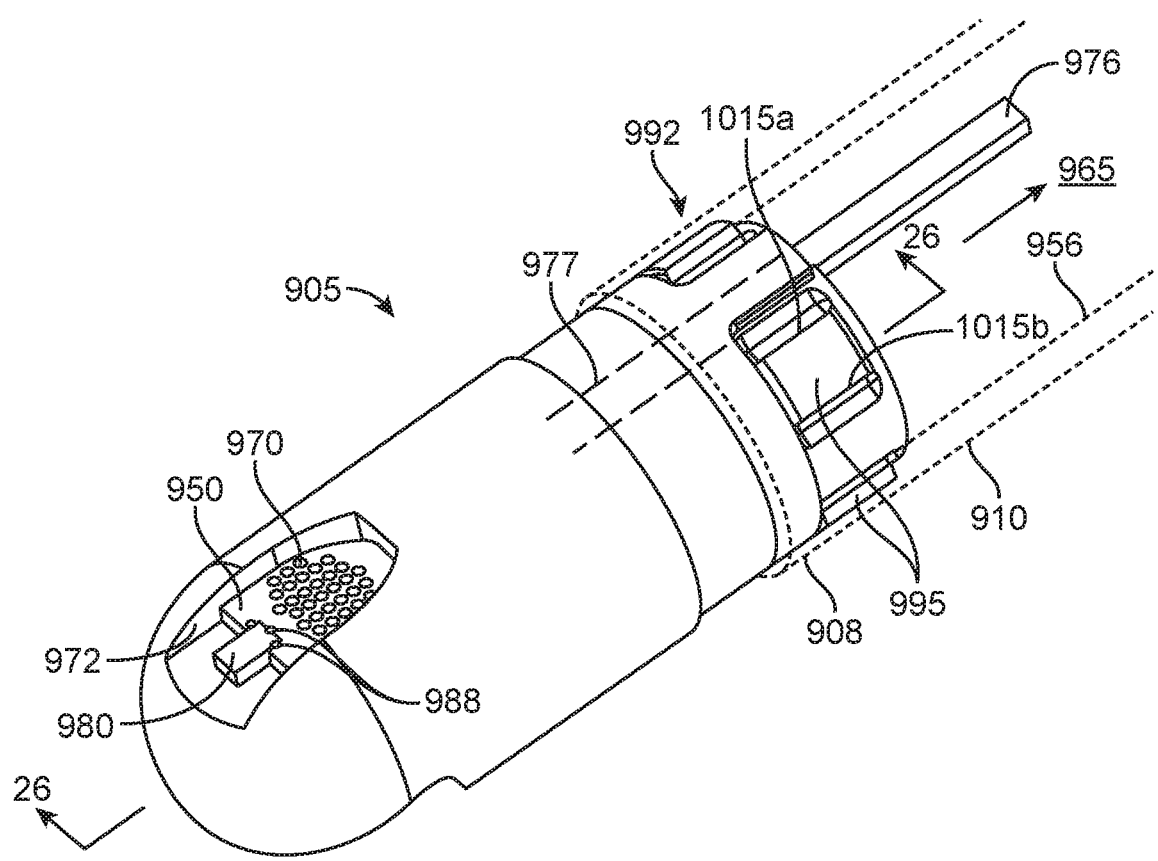
FIG. 25B is a perspective view of a second side of the ceramic cutting member of FIG. 25A without the outer sleeve.

In the variation of FIGS. 24A-24B, the window 940 communicates with an interior or central channel 960 extending through ceramic body 905 to communicate with bore 956 of inner sleeve 910 which is connected to a negative pressure source 965 (FIG. 25B). As indicated by arrows 966A and 966B in FIG. 24A, the window 940 and its cutting edges 942A and 942B can rotate in either rotational direction or can oscillate with 1-10 rotations and one direction followed by a similar number of rotations in the opposing direction, as controlled by a controller.

Now turning to FIG. 24B, the electrode 950 is disposed 180° from the window 940 in the ceramic body 905, which differs from the previous embodiment. In order to use the electrode 950 to ablate or coagulate tissue, the ceramic body 905 may be rotated to, and stopped, in the configuration shown in FIG. 24B to position the electrode 950 upwardly relative to the stationary outer sleeve 915 and window 920 which is within the view of an endoscope. The return electrode comprises an exterior surface portion of the outer sleeve 915 as described previously. It can be understood from FIG. 24B, that when the electrode 950 is exposed, the ceramic cutting member window 940 will be covered by the portion 968 of outer sleeve 915 that opposes the cut-out opening 920. Thus, fluid outflows will be eliminated through the windows 920 and 940 when the windows are not aligned as in FIG. 24B.

Of particular interest, the electrode 950 is microporous and in one variation has a plurality of micropores or microchannels 970 therein that communicate with the central channel 960 in ceramic body 905 and bore 956 of inner sleeve 910 which is connected to a negative pressure source 965. During use of the working end 900 in a saline-submerged working space at the time the electrode 950 is energized to coagulate or ablate tissue, the negative pressure source 965 can be actuated to draw fluid through the microchannels 970 of the electrode 950 which can eliminate bubble formation about the electrode surface which is very important for endoscopic viewing of the targeted treatment site. The controller further can provide different levels of negative pressure for each of the coagulation mode of operation and the ablation mode of operation, with the coagulation mode using a lower level of negative pressure and fluid outflow through the microchannels 970 and the ablation mode using a higher level of negative pressure and fluid outflows through the microchannels.

In general, the electrode 950 typically has a surface area ranging from 1 mm$^2$ to 10 mm$^2$, and more often the electrode surface area range from 2 mm$^2$ to 5 mm$^2$. In a typical variation, the micropores comprise channels having a diameter ranging between 10 micrometers and 100 micrometers, and more often the micropores have a diameter ranging between 20 micrometers and 50 micrometers.

Figure 26:
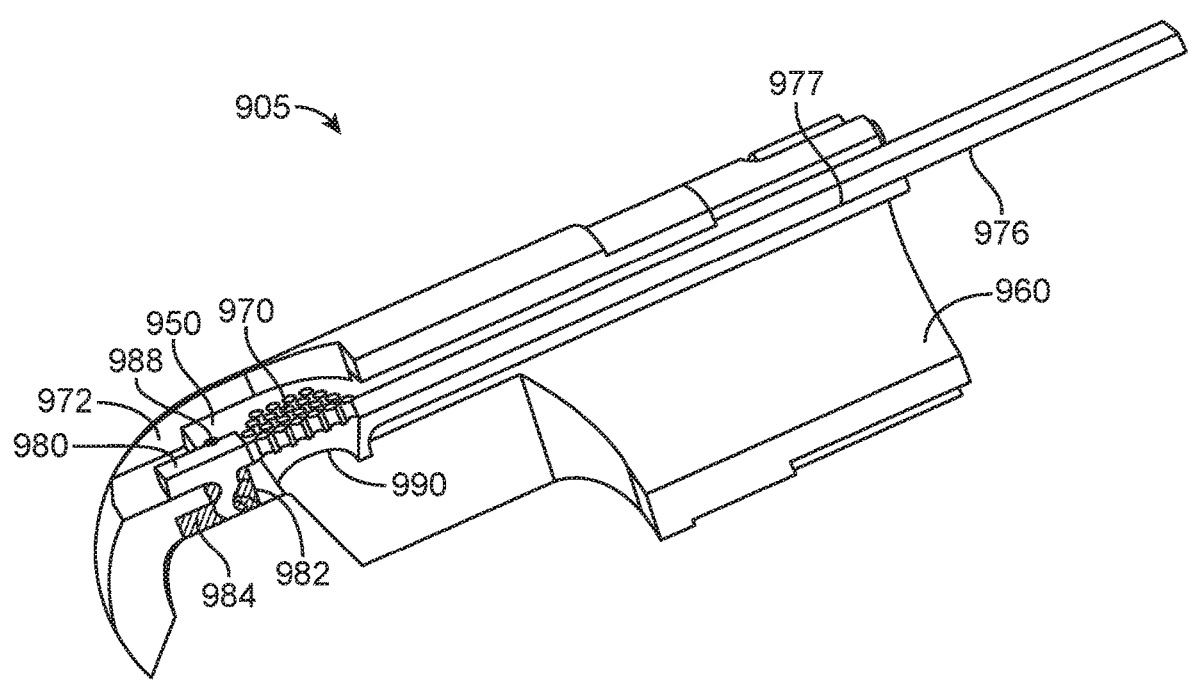
FIG. 26 is a sectional view of the ceramic cutting member of FIG. 25B taken along line 26-26 of FIG. 25B.

Turning to FIGS. 25A, 25B and 26, the method of assembling the electrode 950 and ceramic body 905 can be understood. FIGS. 25A, 25B and 26 all show ceramic body 905 and inner sleeve 910 without the outer sleeve 915. The electrode 950 that is exposed in recess 972 in the ceramic body 905 can be a thin metal such as stainless steel with a proximally-extending leg 976 that extends through a passageway 977 in the ceramic body and is coupled to the inner sleeve 910 which carries current to the electrode 950. The electrode 950 is held in place in the ceramic body 905 by a pin member 980 extends through the ceramic body. As can be seen in FIG. 26, the pin 980 extends through bore 982 and is secured in the ceramic body 905 adhesive or ceramic bonding material 984. The electrode 950 and pin 980 are welded together at weld line indicated at 988. FIG. 26 further shows that micropores 977 are aligned with opening 990 in the wall of the ceramic body 905 to allow the micropores to communicate with the negative pressure source 965.

Now referring again to FIGS. 25A and 25B, the proximal region 992 of ceramic body 905 has a reduced diameter which mates with the bore 956 of inner sleeve 910. The proximal region 992 of ceramic body 905 is further configured with a plurality of projecting portions or features 995 that allow for a mechanical interlock between ceramic body 905 and the inner sleeve 910. A robust and economical connection mechanism between the ceramic body 905 and the metal sleeve 910 is required that does not rely on adhesive bonds, brazing or the like.

Figure 27:
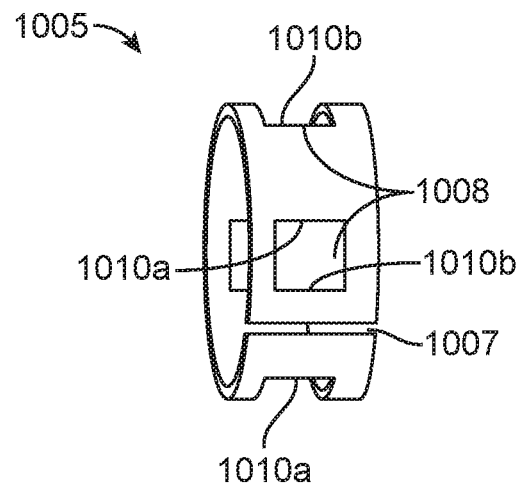
FIG. 27 is a view of a metal collar that comprises a component that allows for mechanical coupling of the ceramic cutting member to the metal inner sleeve.
Figure 28:
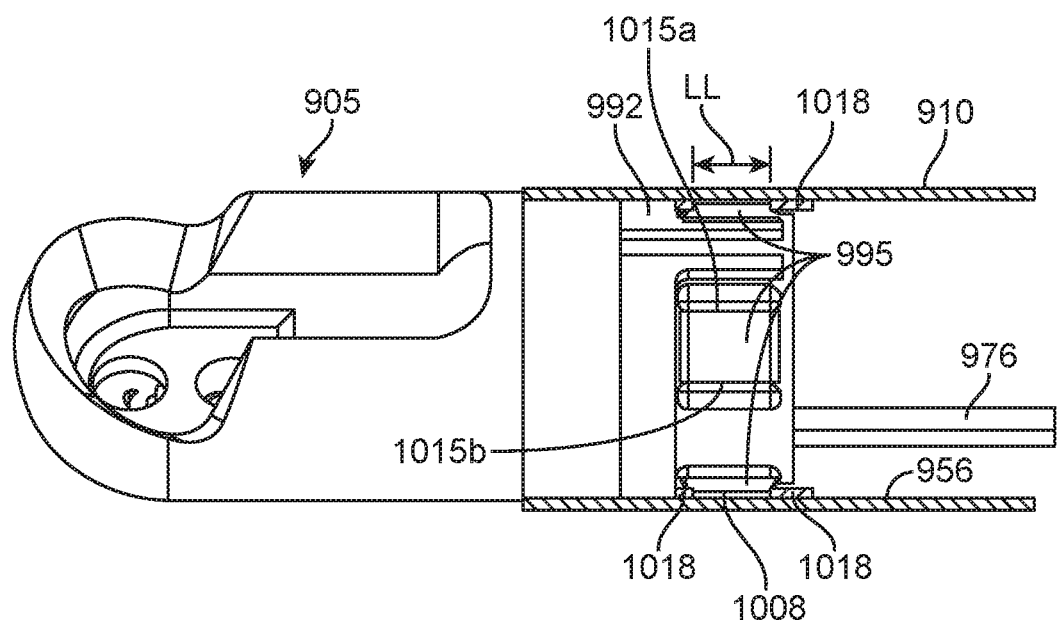
FIG. 28 is a cut-away view of components used and the method of mechanically coupling the ceramic cutting member to the metal inner sleeve

As can be understood from FIGS. 26, 27 and 28, a thin wall metal collar 1005 with receiving openings or slots 1008 for receiving the projecting features 995 can be provided to fit over the reduced diameter proximal region 992 of the ceramic body 905. It can be understood that each receiving opening 1008 has a first and second longitudinal surfaces 1010a and 1010b that interface with longitudinal surfaces 1015a and 1015b of the projecting features 995. The collar 1005 can have an axial discontinuity 1007 to allow it to flex apart to slip over the proximal region 992 and projecting features 995 of the ceramic body. The outer diameter of the metal collar 1005 is dimensioned to fit into the bore 956 of the inner sleeve 910. Thereafter, the inner sleeve 910 can be permanently welded to the metal collar 1005 with welds 1018 provided by laser welding from the exterior of inner sleeve 910. Thus, a reliable and economical mechanical connection can be made between the ceramic body 905 and the metal sleeve 910.

It has been found that a plurality of projecting features 995 and receiving opening slots 1008 is desired to distribute loads over the ceramic body which can be subject to substantial torque, such as when operating in an oscillating mode and the ceramic body engages bone or other hard tissue. The number of projecting features 995 and slots 1008 typically ranging from 2 to 100 and more often from 4 to 10.

The projecting features and slots also may take the form of a spline connection. Typically, the connection provides a minimum length LL of the longitudinal surfaces 1010a, 1010b, 1015a and 1015b that is at least 1 mm and often 2 mm or more. In general, the connection between the ceramic body 905 and the metal inner sleeve 910 includes from 4 to 100 interfacing longitudinal surfaces each having a length of at least 1 mm or at least 2 mm, wherein such surfaces are distributed around the circumference of the ceramic body and sleeve.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

What is claimed is:

1. A method for treating tissue in a patient, the method comprising:
    positioning a distal end of a shaft of a shaver at a treatment site submerged in a conductive fluid so that an outer window of an outer sleeve of the shaft is engaged against a tissue at the treatment site;
    rotating an inner sleeve of the shaft within the outer sleeve so that an inner window of the inner sleeve rotates relative to the outer window to shear the tissue engaged by the outer window, the inner sleeve carrying an electrode thereon that is circumferentially spaced apart from the inner window around the inner sleeve;
    stopping rotation of the inner sleeve within the outer sleeve so that the electrode is exposed in the outer window; and
    delivering electrical current through the exposed electrode to electrosurgically treat the tissue at the treatment site,
    wherein the electrode includes micropores therein that communicate with a central channel in the inner sleeve and a negative pressure source.

2. The method of claim 1, wherein the electrical current is radiofrequency current delivered to cauterize or ablate the tissue at the treatment site that has been sheared by said rotating.

3. The method of claim 1 further comprising applying negative pressure to the micropores during said delivering to inhibit bubble formation at a surface of the electrode.

4. The method of claim 1, wherein the inner window includes a first sharp cutting edge opposite a second sharp cutting edge of the inner window, and wherein said rotating includes rotating the inner sleeve in opposing rotational directions.

5. The method of claim 1, wherein the electrode is circumferentially spaced apart from the inner window by 180°.

6. The method of claim 1, wherein said stopping rotation comprises automatically stopping rotation of the inner sleeve to center the electrode in the outer window.

7. The method of claim 6, wherein said automatically stopping rotation of the inner sleeve comprises sensing a rotational position of the inner sleeve and stopping rotation of the inner sleeve in response to a signal from a controller.

8. The method of claim 1 further comprising actuating the negative pressure source during said delivering to draw an amount of the conductive fluid into the central channel through the micropores.

9. The method of claim 8, wherein said actuating delivers the amount of the conductive fluid to a collection reservoir that is connected to the central channel.

10. The method of claim 1 further comprising applying negative pressure to the central channel during said delivering to draw an amount of the conductive fluid out of the treatment site and into the central channel through the micropores.

11. The method of claim 1, wherein the micropores have diameters in the range of 10 micrometers to 100 micrometers.

12. A method for treating tissue in a patient, the method comprising:
    positioning a distal end of a shaft of a shaver at a treatment site submerged in a conductive fluid, the shaft including an outer sleeve with a distal outer window, the shaft further including an inner sleeve rotatable within the outer sleeve, the inner sleeve including a distal inner window and an electrode circumferentially spaced apart from the distal inner window around the inner sleeve, the electrode including micropores therein that communicate with a central channel in the inner sleeve, wherein said positioning includes the inner sleeve oriented within the outer sleeve so that the electrode is exposed in the distal outer window;
    delivering electrical current through the exposed electrode to electrosurgically treat tissue at the treatment site; and
    applying a negative pressure to the central channel during said delivering to draw an amount of the conductive fluid out of the treatment site and into the central channel through the micropores.

13. The method of claim 12, wherein the electrical current is radiofrequency current.

14. The method of claim 12, wherein said applying is effective to inhibit bubble formation at a surface of the electrode.

15. The method of claim 12, wherein the distal inner window includes at least a first sharp window cutting edge.

16. The method of claim 12, wherein the electrode is circumferentially, spaced apart from the distal inner window by 180°.

17. The method of claim 12, wherein said positioning includes the inner sleeve rotationally stopped within the outer sleeve to center the electrode in the distal outer window.

18. The method of claim 12, wherein said positioning includes sensing a rotational position of the inner sleeve within the outer sleeve and automatically stopping rotation of the inner sleeve in response to a signal from a controller.

19. The method of claim 12, wherein the central channel is connected to a collection reservoir such that said applying delivers the amount of the conductive fluid from the central channel to the collection reservoir.

20. The method of claim 12, wherein the micropores have diameters in the range of 10 micrometers to 100 micrometers.

\* \* \* \* \*